United States Patent
Nakayama et al.

(10) Patent No.: US 7,867,690 B2
(45) Date of Patent: Jan. 11, 2011

(54) TERTIARY ALCOHOL DERIVATIVE, POLYMER COMPOUND AND PHOTORESIST COMPOSITION

(75) Inventors: Osamu Nakayama, Tainai (JP); Ichihiro Aratani, Tainai (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 120 days.

(21) Appl. No.: 12/279,770

(22) PCT Filed: Feb. 16, 2007

(86) PCT No.: PCT/JP2007/052891
§ 371 (c)(1), (2), (4) Date: Aug. 18, 2008

(87) PCT Pub. No.: WO2007/094473
PCT Pub. Date: Aug. 23, 2007

(65) Prior Publication Data
US 2009/0035700 A1    Feb. 5, 2009

(30) Foreign Application Priority Data
Feb. 17, 2006  (JP) .............................. 2006-041359

(51) Int. Cl.
G03F 7/004 (2006.01)
C08F 124/00 (2006.01)
C07D 307/00 (2006.01)
C07D 309/00 (2006.01)
C07C 69/74 (2006.01)

(52) U.S. Cl. .................. 430/270.1; 430/910; 526/266; 526/270; 549/356; 549/429; 560/205; 560/220

(58) Field of Classification Search .............. 430/270.1, 430/910; 526/266, 270; 549/356, 429; 560/205, 560/220
See application file for complete search history.

(56) References Cited

U.S. PATENT DOCUMENTS

2003/0148210 A1 * 8/2003 Funaki et al. ............ 430/270.1

FOREIGN PATENT DOCUMENTS

| | | |
|---|---|---|
| EP | 0 448 978 A2 | 10/1991 |
| EP | 0 448 978 A3 | 10/1991 |
| JP | 5 88367 | 4/1993 |
| JP | 9 73173 | 3/1997 |
| JP | 2003 76023 | 3/2003 |
| JP | 2004 250708 | 9/2004 |
| JP | 2005 239828 | 9/2005 |
| JP | 2005 350527 | 12/2005 |

OTHER PUBLICATIONS

Wipf P et al., "Synthesis and Reactivity of Dioxycarbenium Ions from Epoxy Esters and Cationic Zirconium Complexes", Journal of Organic Chemistry, vol. 58, pp. 5880-5882, (1993).

* cited by examiner

Primary Examiner—John S Chu
(74) Attorney, Agent, or Firm—Oblon, Spivak, McClelland, Maier & Neustadt, L.L.P.

(57) ABSTRACT

(1) A polymer compound for photoresist compositions which is high in storage stability and small swelling at the development and (2) a compound which is a raw material for such a polymer compound are provided; and (3) a photoresist composition with improved LWR containing the subject polymer compound are further provided. In detail, [1] a tertiary alcohol derivative represented by the following general formula (1) is provided.

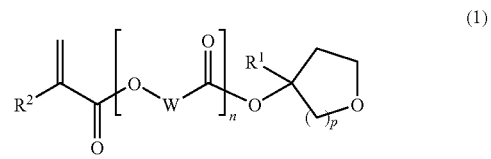

(1)

(In the formula, wherein $R^1$ represents a linear alkyl group having from 1 to 6 carbon atoms, a branched alkyl group having from 3 to 6 carbon atoms or a cyclic alkyl group having from 3 to 6 carbon atoms; $R^2$ represents a hydrogen atom or a methyl group; W represents a linear alkylene group having from 1 to 10 carbon atoms, a branched alkylene group having from 3 to 10 carbon atoms or a cyclic alkylene group having from 3 to 10 carbon atoms; n represents 0 or 1; and p represents 1 or 2.)

5 Claims, No Drawings

TERTIARY ALCOHOL DERIVATIVE, POLYMER COMPOUND AND PHOTORESIST COMPOSITION

TECHNICAL FIELD

The present invention relates to a novel tertiary alcohol derivative, a polymer compound and a photoresist composition. The tertiary alcohol derivative and polymer compound of the present invention are useful as a raw material of a photoresist composition. Also, the photoresist composition of the present invention is useful as a photoresist composition for manufacturing an electronic device.

BACKGROUND ART

In recent years, in the electronic device manufacture field represented by the manufacture of integrated circuit devices, a demand for high integration of devices is increasing, and therefore, a photolithography technology for forming a fine pattern is considered to be necessary. For that reason, the development of a photoresist composition adaptive with photolithography using, as exposure light, radiations having a wavelength of not more than 200 nm, for example, an ArF excimer laser (wavelength: 193 nm), an $F_2$ excimer laser (wavelength: 157 nm), etc. is actively carried out, and there have been proposed a number of photoresist compositions of a chemical amplification type composed of an acid dissociable functional group-containing polymer compound and a compound capable of generating an acid upon irradiation with radiations (hereinafter referred to as "exposure") (the latter compound will be hereinafter referred to as "photo acid generator"). This acid dissociable functional group-containing polymer compound is based on a structure in which a part of an alkali easily soluble site of an alkali soluble polymer compound is protected by an appropriate acid dissociable functional group, and the selection of such an acid dissociable functional group is very important in view of regulating a function as the photoresist composition.

As the existing acid dissociable functional group, there are known (1) one having an adamantane structure (see Non-Patent Document 1 and Patent Document 1); (2) one having a tetrahydropyranyl group (see Patent Document 2); and the like.

The acid dissociable functional group is required to be compatible with high reactivity with an acid and stability such that it is not decomposed at the storage. But, though the tetrahydropyranyl group of (2) has an advantage that the reactivity with an acid is high, it lacks in the storage stability so that it involved a defect that a resist pattern cannot be finally formed with good precision.

Also, one of serious problems of the photolithography technology of recent years includes line width fluctuation of a pattern to be formed, which is called "line width roughness" (hereinafter referred to as "LWR"), and it is required that its tolerable value is less than 8% of the line width (see Non-Patent Document 2). In order to improve LWR, it is necessary that pattern deformation to be caused due to swelling is suppressed, namely a polymer compound which is a component of a photoresist composition is hardly swollen.

A polymer compound in which a group having the adamantane structure of (1) is introduced as an acid dissociable functional group has high reactivity with an acid and storage stability. But, the subject polymer compound is high in hydrophobicity and not sufficient in affinity with a developing solution and forms a portion which does not lead to dissolution in an exposed area at the development, thereby causing swelling. As a result, there is caused a problem that LWR is large. For that reason, the development of a polymer compound for photoresist compositions which is more hardly swollen is still desired earnestly, and it is the present situation that the development of an acid dissociable functional group-containing compound for achieving it is strongly desired earnestly.

Non-Patent Document 1: *Journal of Photopolymer Science and Technology*, Vol. 9, No. 3, 475 to 487 (1996)
Patent Document 1: JP-A-9-73173
Patent Document 2: JP-A-5-88367
Non-Patent Document 2: *International Technology Roadmap for Semiconductors (ITRS)* 2006, "Lithography", page 7

DISCLOSURE OF THE INVENTION

Problems that the Invention is to Solve

As a result of extensive and intensive investigations while paying attention to an acid dissociable functional group of an acid dissociable functional group-containing compound for the purpose of solving the foregoing problems, the present invention has been made. An object of the present invention is to provide (1) a polymer compound for photoresist compositions which is high in reactivity with an acid and storage stability and small swelling at the development; (2) a compound which is a raw material for such a polymer compound; and (3) a photoresist composition with improved LWR comprising the subject polymer compound.

The present inventors made extensive and intensive investigations regarding a relationship among structures and physical properties of various polymer compounds for photoresist compositions and swelling properties at the development. As a result, the present inventors have found out (1) the matter that when a polymer compound for photoresist compositions having a high dissolution rate to a developing solution after exposure is used, swelling can be suppressed; (2) a polymer compound for photoresist compositions having a specified constitutional unit, which has a high dissolution rate to a developing solution after exposure; and (3) a compound having a specified acid dissociable functional group, which is useful as a raw material of the subject polymer compound, leading to accomplishment of the present invention.

Means for Solving the Problems

The present invention is concerned with:

[1] A tertiary alcohol derivative represented by the following general formula (1) (hereinafter referred to as "tertiary alcohol derivative (1)"):

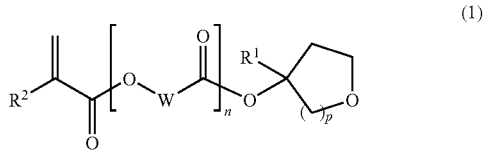

(1)

(In the formula, $R^1$ represents a linear alkyl group having from 1 to 6 carbon atoms, a branched alkyl group having from 3 to 6 carbon atoms or a cyclic alkyl group having from 3 to 6 carbon atoms; $R^2$ represents a hydrogen atom or a methyl group; W represents a linear alkylene group having from 1 to 10 carbon atoms, a branched alkylene group having from 3 to 10 carbon atoms or a cyclic alkylene group having from 3 to 10 carbon atoms; n represents 0 or 1; and p represents 1 or 2);

[2] The tertiary alcohol derivative (1), wherein W is a methylene group or a 1,1-ethanediyl group;

[3] The tertiary alcohol derivative (1), wherein n is 0;

[4] A polymer compound obtained by polymerizing the tertiary alcohol derivative (1) as one of raw materials; and

[5] A photoresist composition comprising the polymer compound as set forth in [4] and a photo acid generator.

Advantages of the Invention

According to the present invention, it is possible to provide (1) a polymer compound for photoresist compositions, which has a high dissolution rate to a developing solution after exposure and which is small swelling at the development; (2) a compound which is a raw material of the subject polymer compound; and (3) a photoresist composition containing the subject polymer compound, which is improved in LWR and which is excellent in storage stability.

BEST MODES FOR CARRYING OUT THE INVENTION

In the formula, examples of the linear alkyl group having from 1 to 6 carbon atoms, the branched alkyl group having from 3 to 6 carbon atoms or the cyclic alkyl group having from 3 to 6 carbon atoms, each of which is represented by $R^1$, include a methyl group, an ethyl group, an n-propyl group, an isopropyl group, an n-butyl group, an isobutyl group, a sec-butyl group, an n-pentyl group, an n-hexyl group, a cyclopropyl group, a cyclobutyl group, a cyclopentyl group and a cyclohexyl group.

In the formula, examples of the linear alkylene group having from 1 to 10 carbon atoms, the branched alkylene group having from 3 to 10 carbon atoms or the cyclic alkylene group having from 3 to 10 carbon atoms, each of which is represented by W, include a methylene group, an ethane-1,1-diyl group, an ethane-1,2-diyl group, a propane-1,1-diyl group, a propane-1,2-diyl group, a propane-1,3-diyl group, a pentane-1,5-diyl group, a hexane-1,1-diyl group and a cyclohexane-1,4-diyl group. Of these, a methylene group and an ethane-1,1-diyl group are preferable.

Specific examples of the tertiary alcohol derivative (1) include the following formulae (1-a) to (1-n):

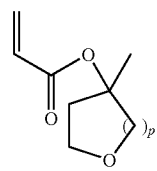
(1-a)

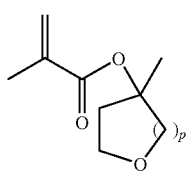
(1-b)

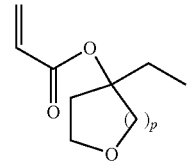
(1-c)

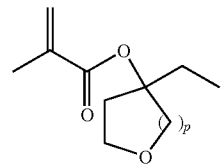
(1-d)

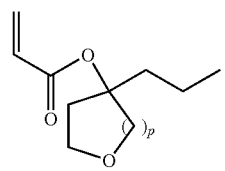
(1-e)

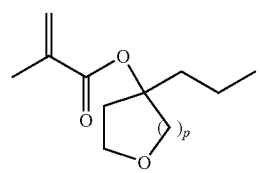
(1-f)

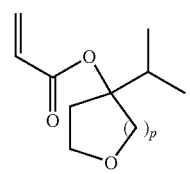
(1-g)

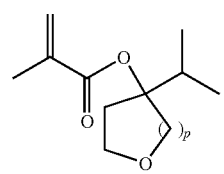
(1-h)

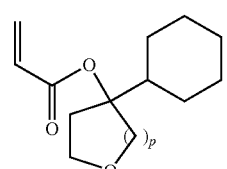
(1-i)

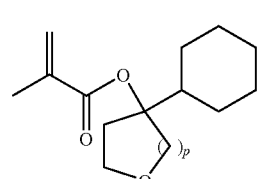
(1-j)

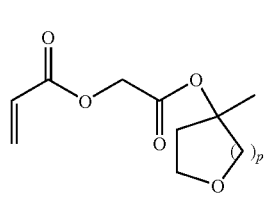
(1-k)

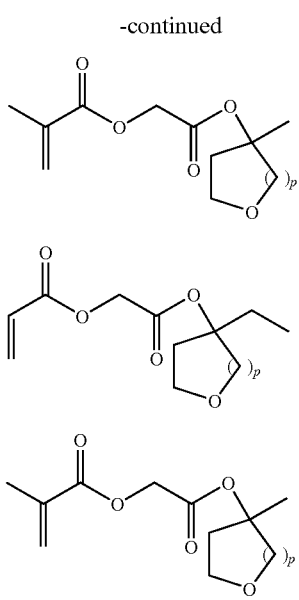

(In the Formulae, p Represents 0 or 1.)

But, it should not be construed that the present invention is limited thereto.

Though a manufacturing method of the tertiary alcohol derivative (1) is not particularly limited, when n of the tertiary alcohol derivative (1) is 0, for example, in case of (1-a) to (1-j) in the specific examples, the manufacturing method is carried out by allowing a tertiary alcohol represented by the following formula (2) (hereinafter referred to as "tertiary alcohol (2)"):

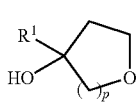

(in the formula, $R^1$ is the same as defined above), to react with a compound represented by a general formula: $CH_2=CR^2COX^1$ (in the formula, $R^2$ is the same as defined above; and $X^1$ represents a chlorine atom, a bromine atom or an iodine atom); a general formula: $(CH_2=CR^2CO)_2O$ (in the formula, $R^2$ is the same as defined above); a general formula: $CH_2=CR^2COOC(=O)R^3$ (in the formula, $R^2$ is the same as defined above; and $R^3$ represents a t-butyl group or a 2,4,6-trichlorophenyl group); or a general formula: $CH_2=CR^2COOSO_2R^4$ (in the formula, $R^2$ is the same as defined above; and $R^4$ represents a methyl group or a p-tolyl group) (such a compound will be hereinafter referred to "polymerizable group introducing agent A") in the presence of a basic substance (this reaction will be hereinafter referred to as "Reaction A").

When n of the tertiary alcohol derivative (1) is 1, for example, in case of (1-k) to (1-n) in the specific examples, the manufacturing method is carried out by allowing the tertiary alcohol (2) to react with a compound represented by a general formula: $X^1—W—COX^1$ (in the formula, W and $X^1$ are the same as defined above); a general formula: $(X^1—W—C(=O))_2O$ (in the formula, W and $X^1$ are the same as defined above); a general formula: $X^1—W—COOC(=O)R^3$ (in the formula, $R^3$, W and $X^1$ are the same as defined above); or a general formula: $X^1—W—COOSO_2R^4$ (in the formula, $R^4$, W and $X^1$ are the same as defined above) (such a compound will be hereinafter referred to "connecting group introducing agent $B_1$") in the presence of a basic substance (this reaction will be hereinafter referred to as "Reaction B-1"); and subsequently allowing a reaction product to react with a compound represented by a general formula: $CH_2=CR^2COOM$ (in the formula, $R^2$ is the same as defined above; and M represents an alkali metal atom, for example, a sodium atom, a potassium atom, etc.) (such a compound will be hereinafter referred to "polymerizable group introducing agent $B_2$") (this reaction will be hereinafter referred to as "Reaction B-2").

Each of the reactions is hereunder described.

The tertiary alcohol (2) to be used in the Reaction A can be manufactured from an easily available raw material. 3-Hydroxy-3-methyltetrahydrofuran can be manufactured by, for example, allowing 3-methyl-3-buten-1-ol to react with hydrogen peroxide in the presence of zeolite (see JP-A-2001-39965).

Also, 4-hydroxy-4-methyltetrahydropyran can be easily manufactured by, for example, subjecting 5,6-dihydro-4-methyl-2H-pyran to a hydration reaction in the presence of an acid, for example, a 35% sulfuric acid aqueous solution, etc.

The tertiary alcohol (2) other than 3-hydroxy-3-methyltetrahydrofuran and 4-hydroxy-4-methyltetrahydropyran can be easily manufactured by, for example, allowing 3-oxotetrahydrofuran or 4-oxotetrahydropyran to react with a reacting agent represented by a formula: $R^1MgX^2$ (in the formula, $R^1$ is the same as defined above; and $X^2$ represents a chlorine atom or a bromine atom).

Specific examples of the polymerizable group introducing agent A represented by the general formula: $CH_2=CR^2COX^1$, which is used in the Reaction A, include acryloyl chloride and methacryloyl chloride. Specific examples of the polymerizable group introducing agent A represented by the general formula: $(CH_2=CR^2CO)_2O$ include acrylic anhydride and methacrylic anhydride. Specific examples of the polymerizable group introducing agent A represented by the general formula: $CH_2=CR^2COOC(=O)R^3$ include acrylic pivalic anhydride, acrylic 2,4,6-trichlorobenzoic anhydride, methacrylic pivalic anhydride and methacrylic 2,4,6-trichlorobenzoic anhydride. Specific examples of the polymerizable group introducing agent A represented by the general formula: $CH_2=CR^2COOSO_2R^4$ include acrylic methanesulfonic anhydride, acrylic p-toluenesulfonic anhydride, methacrylic methanesulfonic anhydride and methacrylic p-toluenesulfonic anhydride.

From the viewpoints of economy and easiness of post-treatment, the use amount of the polymerizable group introducing agent A is preferably in the range of from 0.8 to 5 moles, and more preferably in the range of from 0.8 to 3 moles per mole of the tertiary alcohol (2).

Examples of the basic substance to be used in the Reaction A include inorganic bases, for example, sodium hydride, potassium hydride, sodium hydroxide, potassium hydroxide, sodium carbonate, potassium carbonate, etc.; and organic bases, for example, triethylamine, 4-(N,N-dimethylamino)pyridine, N,N-dimethylaniline, pyridine, tributylamine, diazabicyclo[2,2,2]octane, etc. These may be used singly or may be used in admixture of two or more kinds thereof. From the viewpoints of economy and easiness of post-treatment, the use amount of the basic substance is preferably in the range of from 0.8 to 5 moles, and more preferably in the range of from 0.8 to 3 moles per mole of the tertiary alcohol (2).

The Reaction A can be carried out in the presence or absence of a solvent. The solvent is not particularly limited so far as it does not adversely affect the reaction, and examples thereof include ethers, for example, diethyl ether, diisopropyl ether, tetrahydrofuran, etc.; aliphatic hydrocarbons, for example, hexane, heptane, octane, etc.; halogenated hydrocarbons, for example, methylene chloride, 1,2-dichloroethane, etc.; aromatic hydrocarbons, for example, toluene, xylene, cymene, etc.; N,N-dimethylformamide; and dimethyl sulfoxide. These may be used singly or may be used in admixture of two or more kinds thereof. In case of using a solvent, though the use amount thereof is not limited, in general, it is preferably in the range of from 0.1 to 20 parts by mass, and more preferably in the range of from 0.1 to 10 parts by mass per part by mass of the tertiary alcohol (2).

The Reaction A is carried out preferably at a temperature in the range of from −80 to 100° C., and more preferably at a temperature in the range of from −50 to 80° C. Also, the reaction time varies depending upon the kind and use amount of the tertiary alcohol (2) or polymerizable group introducing agent A, the kind and use amount of the basic substance, the kind and use amount of the solvent, the reaction temperature and the like, and it is usually in the range of from 10 minutes to 10 hours.

The Reaction A can be terminated by adding water and/or an alcohol. Examples of such an alcohol include methanol, ethanol, n-propanol and i-propanol. The use amount of water and/or the alcohol may be one mole or more per mole of the excessive amount relative to the tertiary alcohol (2) of the polymerizable group introducing agent A. When the use amount is small, there may be the case where the unreacted polymerizable group introducing agent A cannot be completely decomposed, thereby forming a by-product.

Next, the Reaction B-1 and Reaction B-2 are described.

Specific examples of the connecting group introducing agent $B_1$ represented by the general formula: $X^1$—W—$COX^1$, which is used in the Reaction B-1, include chloroacetyl chloride, 2-chloropropionyl chloride and 2-bromo-2-methylpropionyl bromide. Specific examples of the connecting group introducing agent $B_1$ represented by the general formula: $(X^1$—W—$C(=O))_2O$ include chloroacetic anhydride and 2-chloropropinic anhydride. Specific examples of the connecting group introducing agent $B_1$ represented by the general formula: $X^1$—W—$COOC(=O)R^3$ include chloroacetic pivalic anhydride, chloroacetic 2,4,6-trichlorobenzoic anhydride, 2-chloropropionic pivalic anhydride and 2-chloropropionic 2,4,6-trichlorobenzoic anhydride. Also, specific examples of the connecting group introducing agent $B_1$ represented by the general formula: $X^1$—W—$COOSO_2R^4$ include chloroacetic methanesulfonic anhydride, chloroacetic p-toluenesulfonic anhydride, 2-chloropropionic methanesulfonic anhydride and 2-chloropropionic p-toluenesulfonic anhydride. From the viewpoints of economy and easiness of post-treatment, the use amount of such a connecting group introducing agent $B_1$ is preferably in the range of from 0.8 to 5 moles, and more preferably in the range of from 0.8 to 3 moles per mole of the tertiary alcohol (2).

Examples of the basic substance to be used in the Reaction B-1 include inorganic bases, for example, sodium hydride, potassium hydride, sodium hydroxide, potassium hydroxide, sodium carbonate, potassium carbonate, etc.; and organic bases, for example, triethylamine, 4-(N,N-dimethylamino)pyridine, N,N-dimethylaniline, pyridine, tributylamine, diazabicyclo[2,2,2]octane, etc. These may be used singly or may be used in admixture of two or more kinds thereof. From the viewpoints of economy and easiness of post-treatment, the use amount of the basic substance is preferably in the range of from 0.8 to 5 moles, and more preferably in the range of from 0.8 to 3 moles per mole of the tertiary alcohol (2).

The Reaction B-1 can be carried out in the presence or absence of a solvent. The solvent is not particularly limited so far as it does not adversely affect the reaction, and examples thereof include ethers, for example, diethyl ether, diisopropyl ether, tetrahydrofuran, etc.; aliphatic hydrocarbons, for example, hexane, heptane, octane, etc.; halogenated hydrocarbons, for example, methylene chloride, 1,2-dichloroethane, etc.; aromatic hydrocarbons, for example, toluene, xylene, cymene, etc.; N,N-dimethylformamide; and dimethyl sulfoxide. These may be used singly or may be used in admixture of two or more kinds thereof. In case of using a solvent, though the use amount thereof is not particularly limited, in general, it is preferably in the range of from 0.1 to 20 parts by mass, and more preferably in the range of from 0.1 to 10 parts by mass per part by mass of the tertiary alcohol (2).

The Reaction B-1 is carried out preferably at a temperature in the range of from −80 to 100° C., and more preferably at a temperature in the range of from −50 to 80° C. Also, the reaction time varies depending upon the kind and use amount of the tertiary alcohol (2) or connecting group introducing agent $B_1$, the kind and use amount of the basic substance, the kind and use amount of the solvent, the reaction temperature and the like, and it is usually in the range of from 10 minutes to 10 hours.

The Reaction B-1 can be terminated by adding water and/or an alcohol. Examples of such an alcohol include methanol, ethanol, n-propanol and i-propanol. The use amount of water and/or the alcohol may be one mole or more per mole of the excessive amount relative to the tertiary alcohol (2) of the connecting group introducing agent $B_1$. When the use amount is small, there may be the case where the unreacted connecting group introducing agent $B_1$ cannot be completely decomposed, thereby forming a by-product.

The thus obtained product of the Reaction B-1 can be used in the Reaction B-2 upon being isolated from the reaction mixed solution. Also, it is possible to carry out the Reaction B-2 by adding chemicals to be used in the Reaction B-2 to the subject reaction mixed solution without isolating the product of the Reaction B-1.

Specific examples of the polymerizable group introducing agent $B_2$ to be used in the Reaction B-2 include sodium acrylate, potassium acrylate, sodium methacrylate and potassium methacrylate. From the viewpoints of economy and easiness of post-treatment, the use amount of the polymerizable group introducing agent $B_2$ is preferably in the range of from 0.8 to 5 moles, and more preferably in the range of from 0.8 to 3 moles per mole of the production of the Reaction B-1. The polymerizable group introducing agent $B_2$ may be a commercially available material. Also, it may be generated in a system by adding a corresponding carboxylic acid and an alkali metal hydride or an alkali metal carbonate to the reaction mixture.

In the Reaction B-2, it is preferable to use an activating agent, for example, potassium iodide, sodium iodide, tetrabutylammonium iodide, tetrabutylammonium broide, etc. as the need arises. From the viewpoints of economy and easiness of post-treatment, the use amount of the activating agent is preferably in the range of from 0.001 to 0.5 moles, and more preferably in the range of from 0.005 to 0.3 moles per mole of the product of the Reaction B-1.

The Reaction B-2 can be carried out in the presence or absence of a solvent. The solvent is not particularly limited so far as it does not adversely affect the reaction, and examples thereof include ethers, for example, diethyl ether, diisopropyl ether, tetrahydrofuran, etc.; aliphatic hydrocarbons, for example, hexane, heptane, octane, etc.; halogenated hydrocarbons, for example, methylene chloride, 1,2-dichloroethane, etc.; aromatic hydrocarbons, for example, toluene, xylene, cymene, etc.; amides, for example, N,N-dimethylformamide, N,N-dimethylacetamide, N-methylpyrrolidone, etc.; and dimethyl sulfoxide. These solvents may be used singly or may be used in admixture of two or more kinds thereof. In case of using a solvent, though the use amount thereof is not particularly limited, in general, it is preferably in the range of from 0.1 to 20 parts by mass, and more preferably in the range of from 0.1 to 10 parts by mass per part by mass of the product of the Reaction B-1.

The Reaction B-2 is carried out preferably at a temperature in the range of from −80 to 100° C., and more preferably at a temperature in the range of from −50 to 80° C. Also, the reaction time varies depending upon the kind and use amount of the product of the Reaction B-1 or polymerizable group introducing agent $B_2$, the kind and use amount of the activating agent, the kind and use amount of the basic substance, the kind and use amount of the solvent, the reaction temperature and the like, and it is usually in the range of from 10 minutes to 10 hours.

It is preferable that the tertiary alcohol derivative (1) obtained through the Reaction A or the Reaction B-1 and Reaction B-2 is separated and purified in the usual way as the need arises. For example, after washing with water, the reaction mixture can be purified by a method which is employed for usual separation and purification of an organic compound, for example, concentration, distillation, column chromatography, recrystallization, etc. Also, it is possible to reduce the content of a metal in the obtained tertiary alcohol derivative (1) by a treatment with a chelating agent, for example, nitrilotriacetic acid, ethylenediaminetetraacetic acid, etc.; or a treatment by a metal removal filter, for example, ZETA PLUS (a trade name, manufactured by CUNO Incorporated), PROTEGO (a trade name, manufactured by Nippon Mykrolis K.K.), etc. as the need arises.

The polymer compound of the present invention is a polymer obtained by homopolymerizing the tertiary alcohol derivative (1) or a copolymer obtained by copolymerizing the tertiary alcohol derivative (1) and other polymerizable compound and is useful so far as it has a constitutional unit on the basis of the tertiary alcohol derivative (1). In general, a content proportion of the constitutional unit on the basis of the tertiary alcohol derivative (1) in the polymer compound of the present invention is preferably in the range of from 10 to 80% by mole, and more preferably in the range of from 20 to 70% by mole. Specific examples of the constitutional unit on the basis of the tertiary alcohol derivative (1) include those represented by the following formulae (1'-a) to (1'-x), but it should not be construed that the present invention is limited thereto.

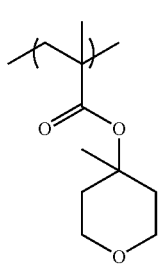
(1'-a)

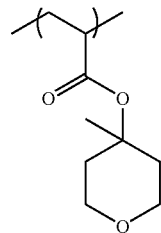
(1'-b)

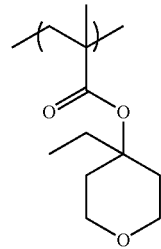
(1'-c)

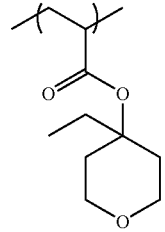
(1'-d)

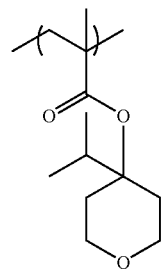
(1'-e)

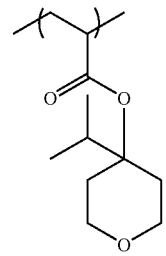
(1'-f)

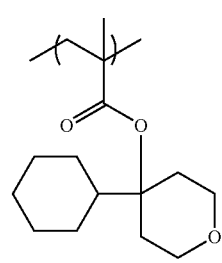
(1'-g)

-continued
(1'-h)
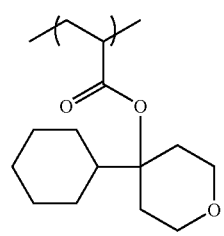
(1'-i)
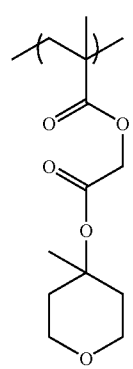
(1'-j)
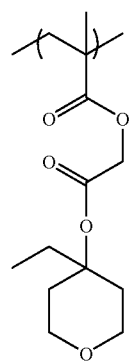
(1'-k)
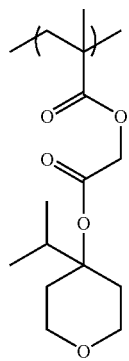
-continued
(1'-l)
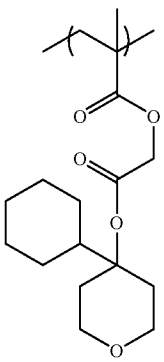
(1'-m)
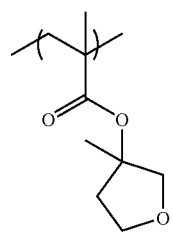
(1'-n)
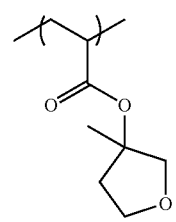
(1'-o)
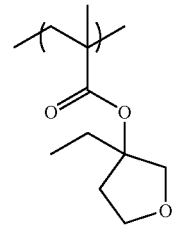
(1'-p)
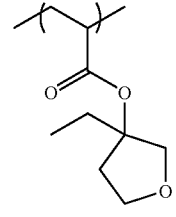
(1'-q)
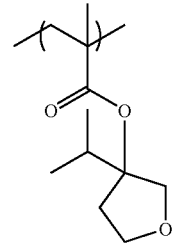

(1'-r) 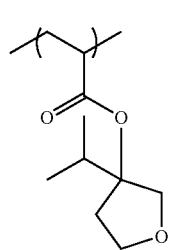
(1'-s) 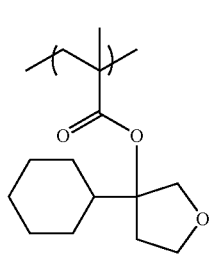
(1'-t) 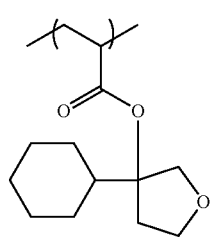
(1'-u) 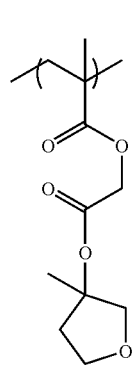
(1'-v) 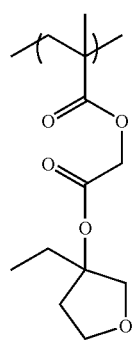
(1'-w) 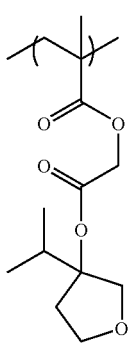
(1'-x) 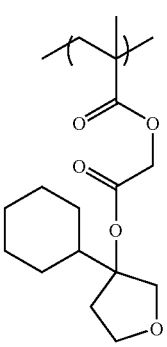
Specific examples of other polymerizable compound which can be copolymerized with the tertiary alcohol derivative (1) (this polymerizable compound will be hereinafter referred to as "copolymerizable monomer (3)") include Compounds (I) to (IX) represented by the following chemical formulae:
(I) 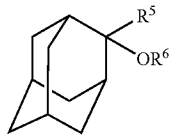
(II) 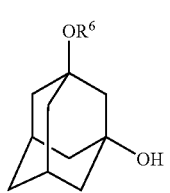
(III) 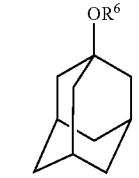
(IV) 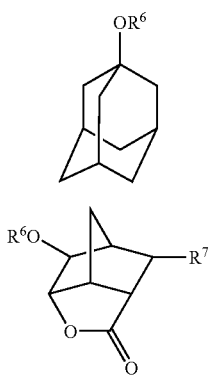

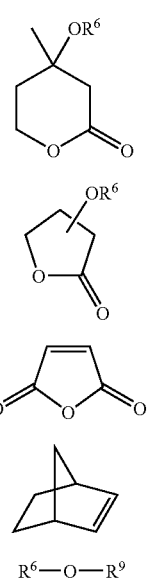

(In the formulae, R⁵ represents a hydrogen atom or an alkyl group having from 1 to 3 carbon atoms; R⁶ represents a polymerizable group; R⁷ represents a hydrogen atom or COOR⁸; R⁸ represents an alkyl group having from 1 to 3 carbon atoms; and R⁹ represents an alkyl group having from 1 to 6 carbon atoms.)

But, it should not be construed that the present invention is limited thereto.

In the copolymerization monomer (3), examples of the alkyl group having from 1 to 3 carbon atoms which is represented independently by each of R⁵ and R⁸ include a methyl group, an ethyl group, an n-propyl group and an isopropyl group. Examples of the alkyl group having from 1 to 6 carbon atoms which is represented by R⁹ include a methyl group, an ethyl group, an n-propyl group, an isopropyl group, an n-butyl group, an isobutyl group, an s-butyl group and a t-butyl group. Also, Examples of the polymerizable group which is represented by R⁶ include an acryloyl group, a methacryloyl group, a vinyl group and a crotonoyl group.

The foregoing polymer compound can be manufactured by radical polymerization according to the usual way. When a polymer compound having small molecular weight distribution is desired, it can also be manufactured by living radical polymerization or the like. The radical polymerization is carried out by polymerizing at least one kind of the tertiary alcohol derivative (1) and optionally, at least one kind of the foregoing copolymerizable monomer (3) in the presence of a radical polymerization initiator and a solvent and optionally, a chain transfer agent. Such radical polymerization is hereunder described.

A method for carrying out the present radical polymerization is not particularly limited, and a customary method for manufacturing, for example, an acrylic polymer compound, including a solution polymerization method, an emulsion polymerization method, a suspension polymerization method and a bulk polymerization method, can be employed.

Examples of the radical polymerization initiator include hydroperoxide compounds, for example, t-butylhydroperoxide, cumene hydroperoxide, etc.; dialkylperoxide compounds, for example, di-t-butylperoxide, t-butyl-α-cumylperoxide, di-α-cumylperoxide, etc.; diacyl peroxide compounds, for example, benzoyl peroxide, diisobutyryl peroxide, etc.; and azo compounds, for example, 2,2'-azobisisobutyronitrile, dimethyl 2,2'-azobisisobutyrate, etc.

Though the use amount of the radical polymerization initiator can be properly chosen according to a polymerization condition, for example, the kind and use amount of each of the tertiary alcohol derivative (1), the copolymerizable monomer (3), the chain transfer agent and the solvent, a polymerization temperature, etc., it is usually in the range of from 0.005 to 0.2 moles, and preferably in the range of from 0.01 to 0.15 moles per mole of the whole of the polymerizable compounds [the total sum of the tertiary alcohol derivative (1) and the copolymerizable monomer (3)].

Examples of the chain transfer agent include thiol compounds, for example, dodecanethiol, mercaptoethanol, mercaptopropanol, mercaptoacetic acid, mercaptopropionic acid, etc. These may be used singly or may be used in admixture of two or more kinds thereof. In case of using a chain transfer agent, the use amount thereof is usually in the range of from 0.005 to 0.2 moles, and preferably in the range of from 0.01 to 0.15 moles per mole of the whole of the polymerizable compounds [the total sum of the tertiary alcohol derivative (1) and the copolymerizable monomer (3)].

In general, the present radical polymerization is carried out in the presence of a solvent. The solvent is not particularly limited so far as it does not adversely affect the reaction, and examples thereof include glycol ethers, for example, propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, etc.; esters, for example, ethyl lactate, methyl 3-methoxypropionate, methyl acetate, ethyl acetate, propyl acetate, etc.; ketones, for example, acetone, methyl ethyl ketone, methyl isopropyl ketone, methyl isobutyl ketone, methyl amyl ketone, cyclopentanone, cyclohexanone, etc.; and ethers, for example, diethyl ether, diisopropyl ether, dibutyl ether, tetrahydrofuran, 1,4-dioxane, etc. The solvent may be used singly or may be used in admixture of two or more kinds thereof.

The use amount of the solvent is usually in the range of from 0.5 to 20 parts by mass, and preferably in the range of from 1 to 10 parts by mass per part by mass of the whole of the polymerizable compounds [the total sum of the tertiary alcohol derivative (1) and the copolymerizable monomer (3)].

The reaction temperature of the present radical polymerization is usually from 40 to 150° C., and from the viewpoint of stability of the polymer compound to be formed, it is preferably in the range of from 60 to 120° C.

Though the reaction time of the present radical polymerization varies depending upon a polymerization condition, for example, the kind and use amount of each of the tertiary alcohol derivative (1), the copolymerizable monomer (3), the radical polymerization initiator and the solvent, a polymerization temperature of the polymerization reaction, etc., in general, it is in the range of from 30 minutes to 48 hours, and more preferably in the range of from one hour to 24 hours.

It is possible to isolate the thus obtained polymer compound (hereinafter referred to as "polymer compound (4)") by a usual operation, for example, reprecipitation, etc. The isolated polymer compound (4) can also be dried by vacuum drying or the like.

Examples of the solvent to be used in the foregoing reprecipitation operation include aliphatic hydrocarbons, for example, pentane, hexane, etc.; alicyclic hydrocarbons, for example, cyclohexane, etc.; aromatic hydrocarbons, for example, benzene, xylene, etc.; halogenated hydrocarbons, for example, methylene chloride, chloroform, chlorobenzene, dichlorobenzene, etc.; nitrated hydrocarbons, for example, nitromethane, etc.; nitrites, for example, acetonitrile, benzonitrile, etc.; ethers, for example, diethyl ether, diisopropyl ether, tetrahydrofuran, 1,4-dioxane, etc.; ketones, for example, acetone, methyl ethyl ketone; carboxylic acids, for example, acetic acid, etc.; esters, for example, ethyl acetate, butyl acetate, etc.; carbonates, for example, dimethyl carbonate, diethyl carbonate, ethylene carbonate, etc.; alcohols, for example, methanol, ethanol, n-propanol, i-propanol, butanol, etc.; and water. These solvents may be used singly or may be used in admixture of two or more kinds thereof.

Though the use amount of the solvent varies depending upon the kind of the polymer compound (4) and the kind of the solvent, in general, it is preferably in the range of from 0.5 to 100 parts by mass, and more preferably in the range of from 1 to 50 parts by mass per part by mass of the polymer compound (4).

Specific examples of the polymer compound (4) include polymer compounds represented by the following chemical structural formulae (in the formulae, $R^{10}$ to $R^{24}$ each independently represents a hydrogen atom or a methyl group; and a, b, c, d and e each represents a molar ratio of each of the constitutional units, with (a+b) being 1 and (c+d+e) being 1), but it should not be construed that the present invention is limited thereto.

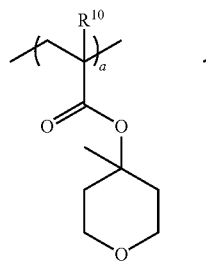
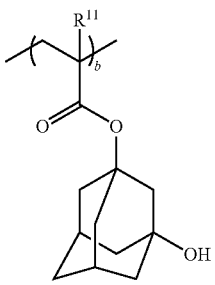
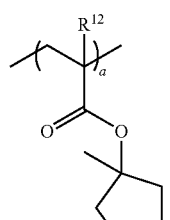
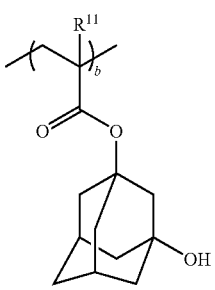
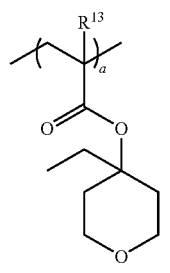
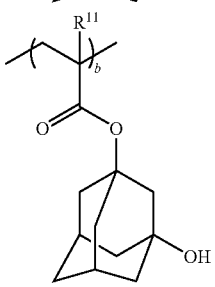

-continued

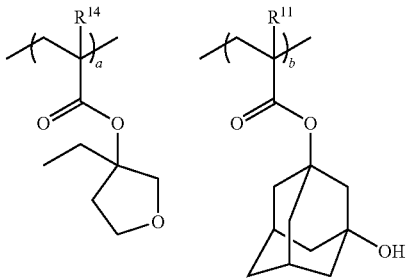
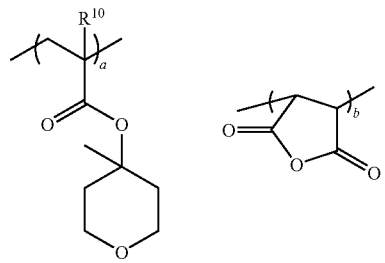
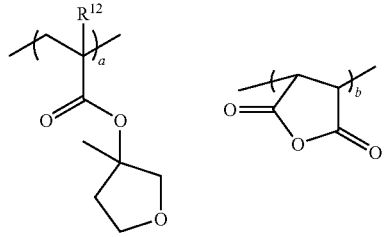
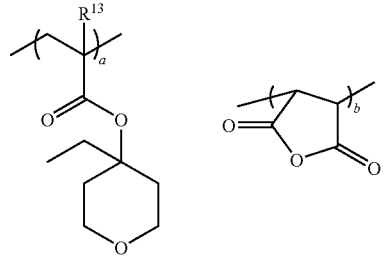
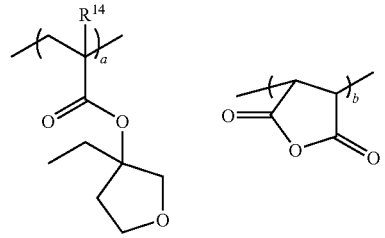
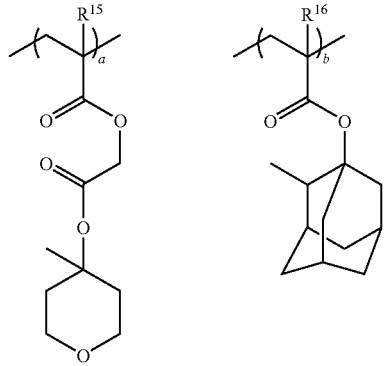

-continued
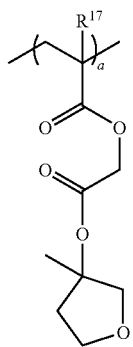 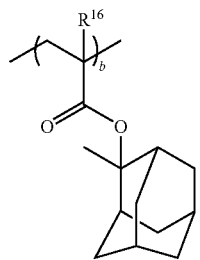
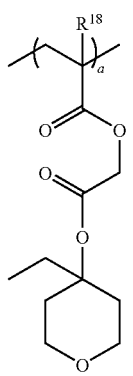 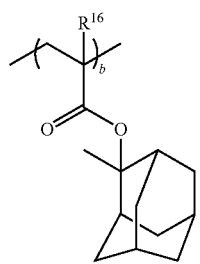
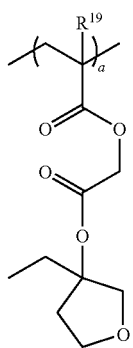 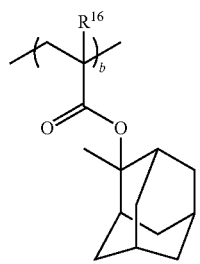
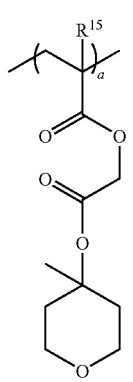 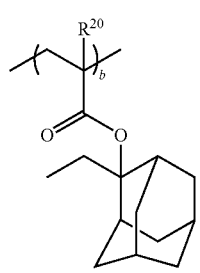
-continued
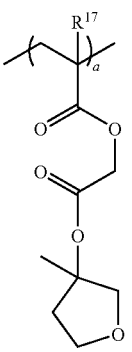 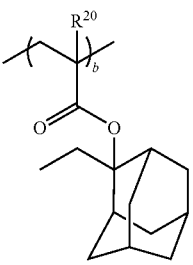
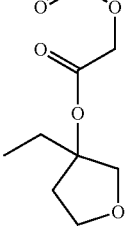 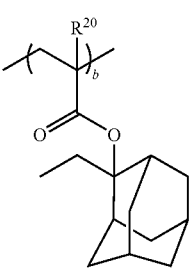
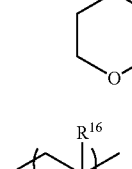 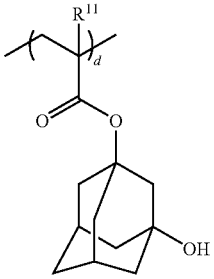
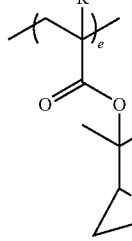 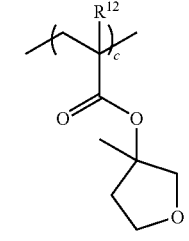

-continued
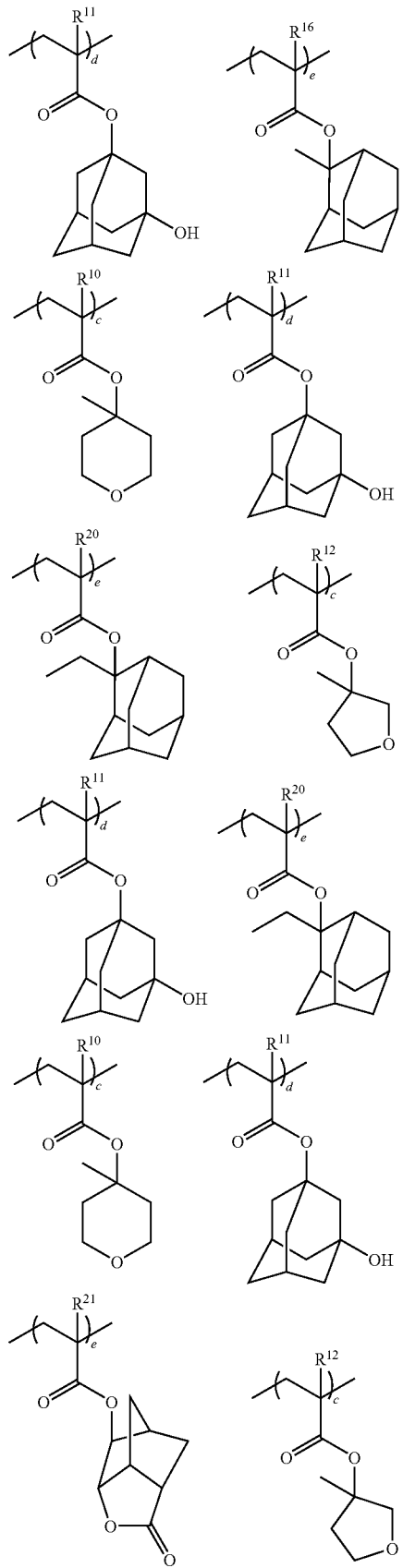
-continued
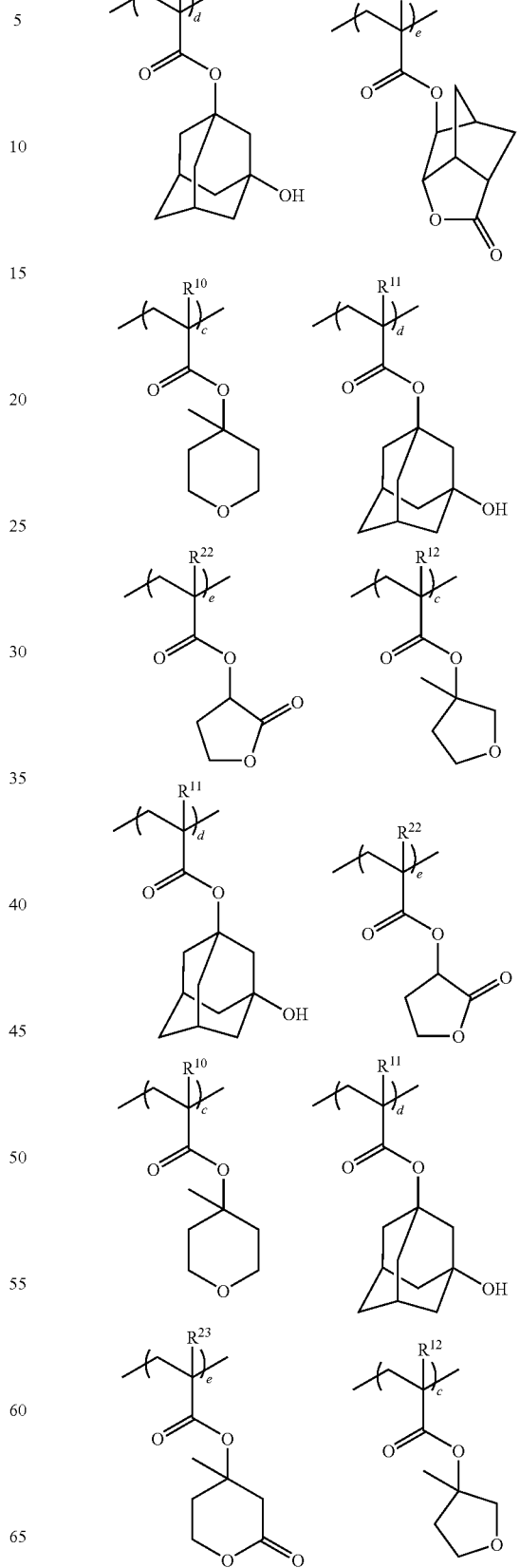

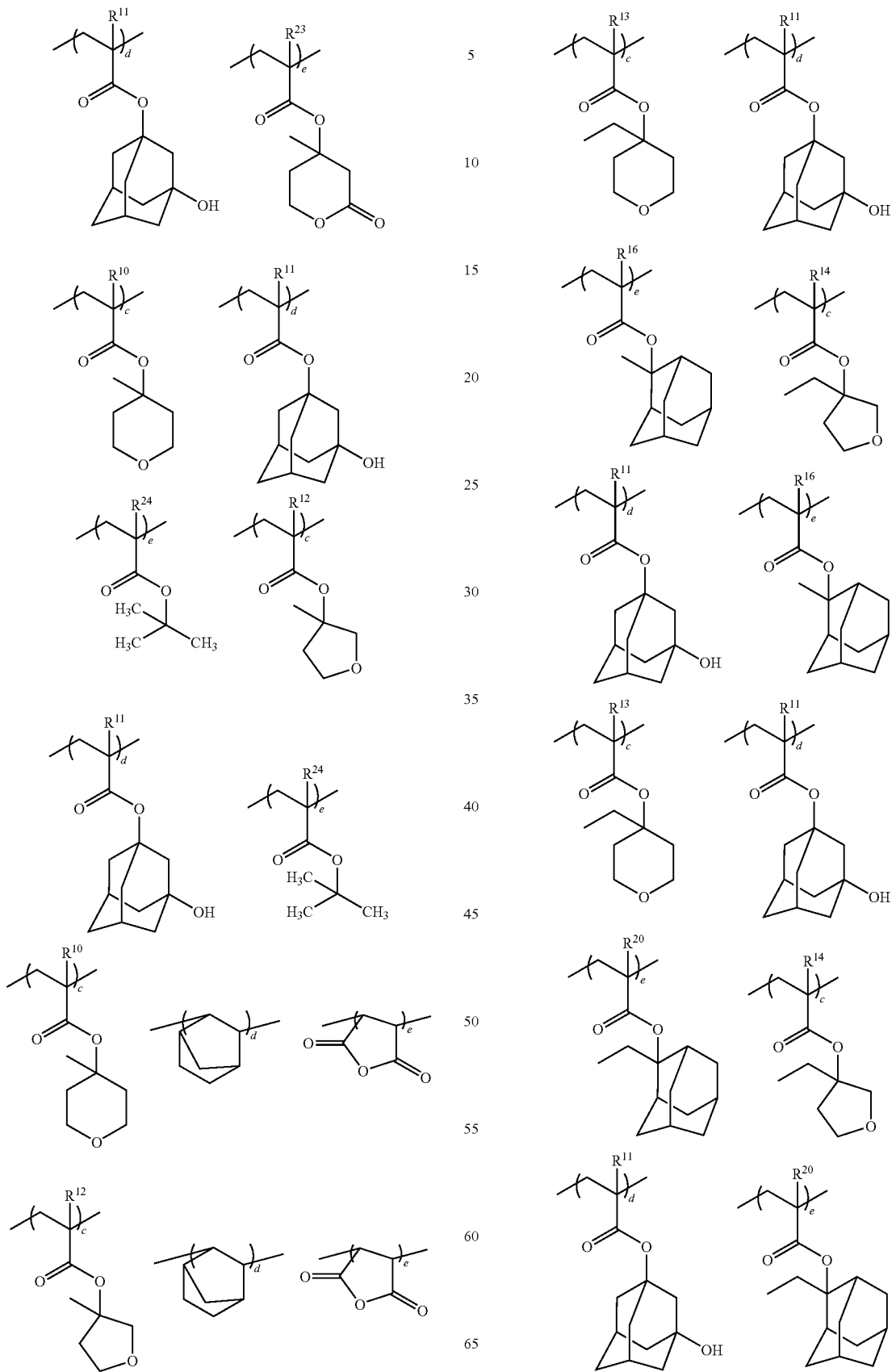

-continued
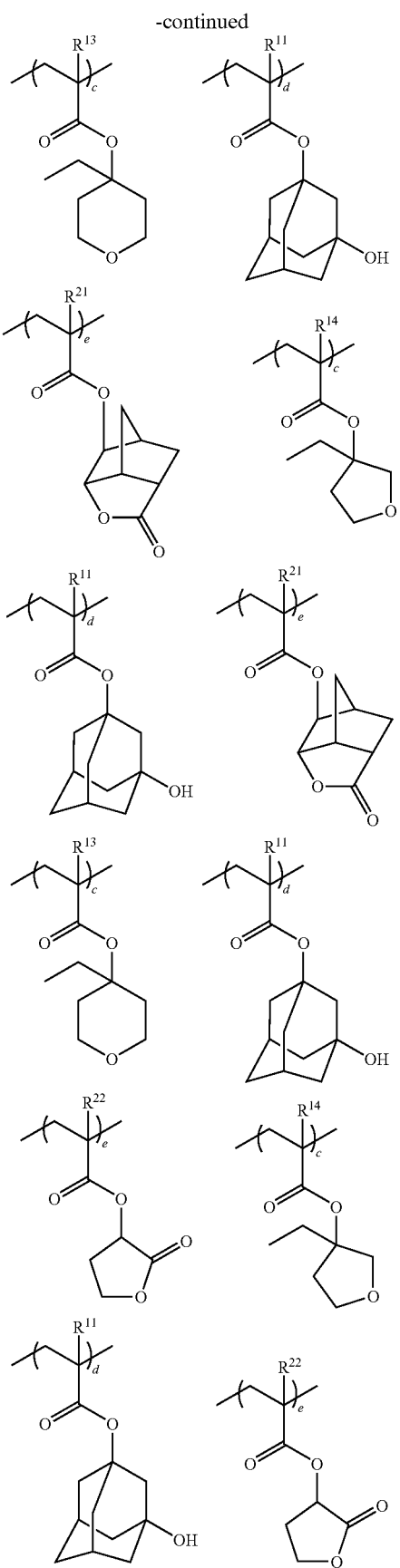
-continued
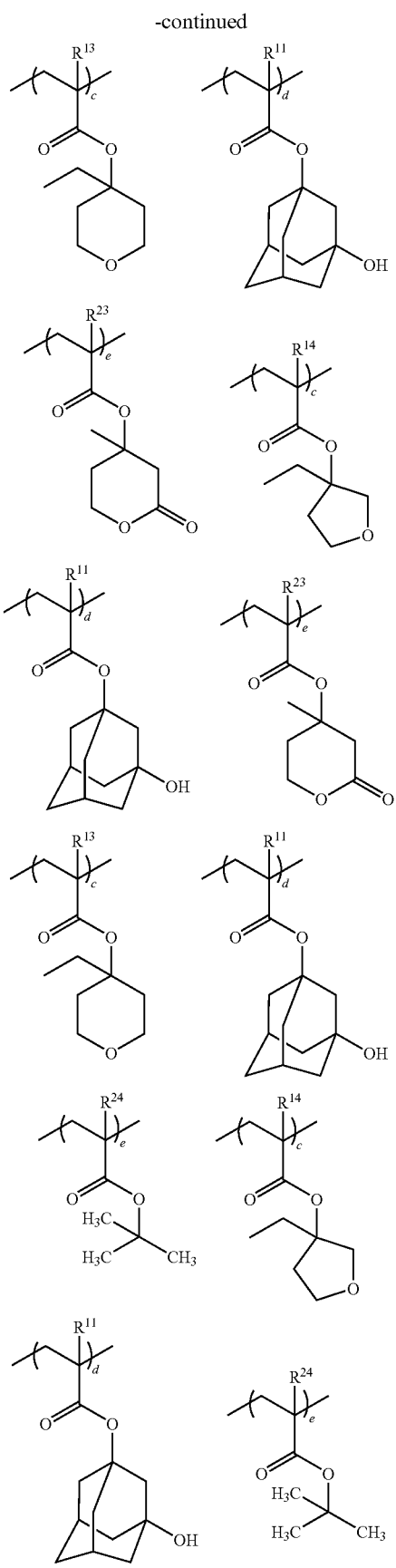

-continued
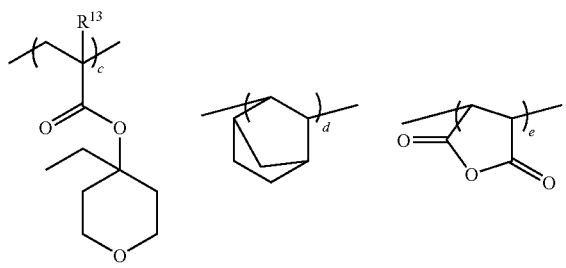
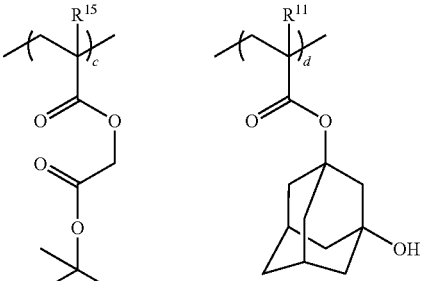
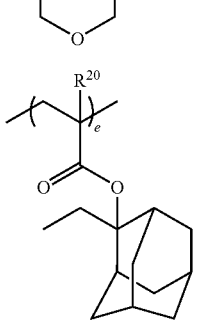
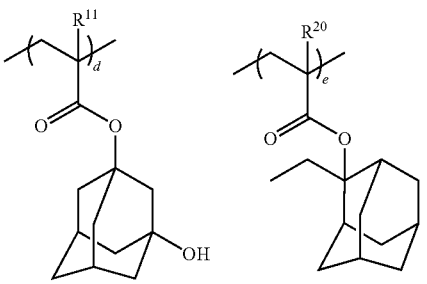
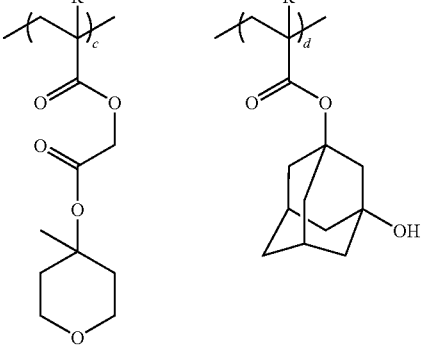
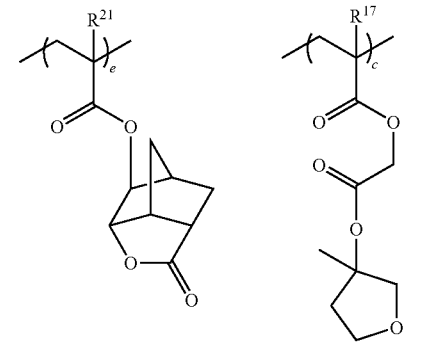

-continued
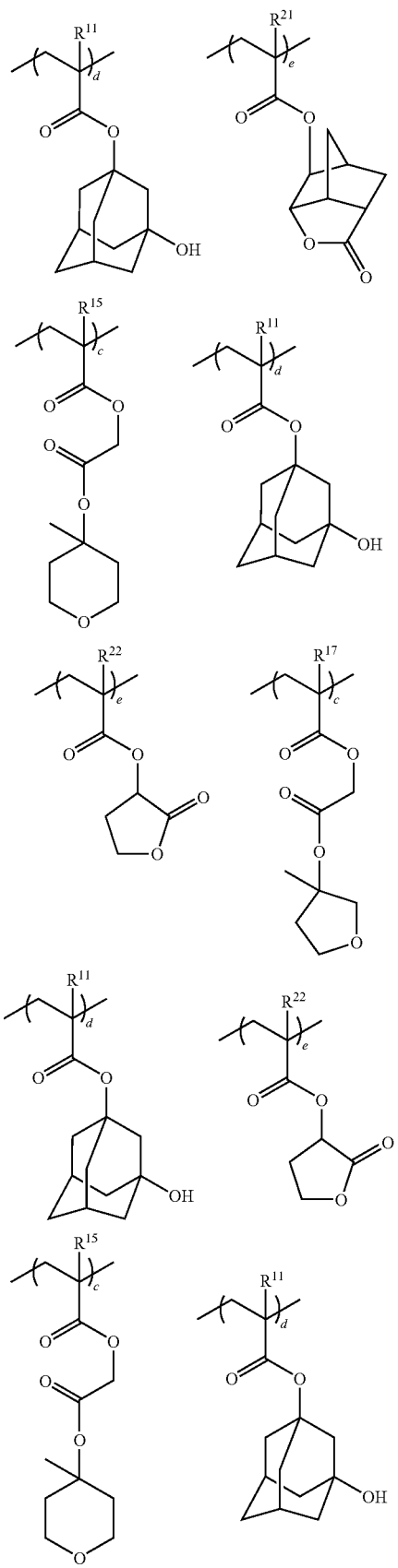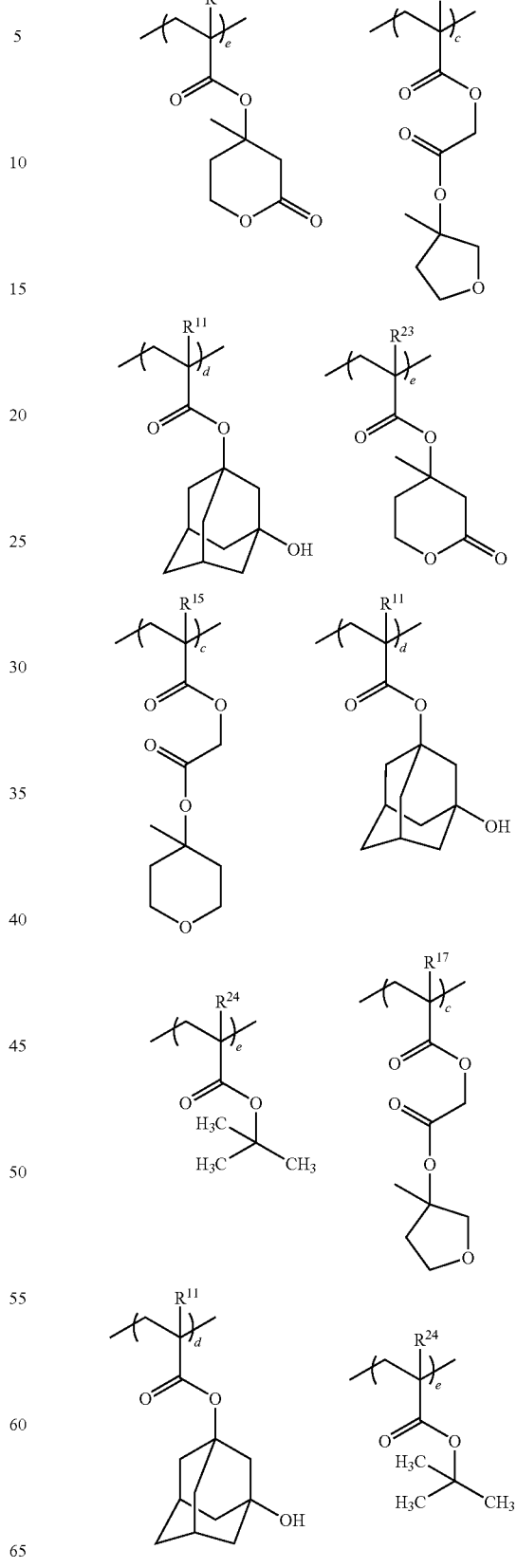

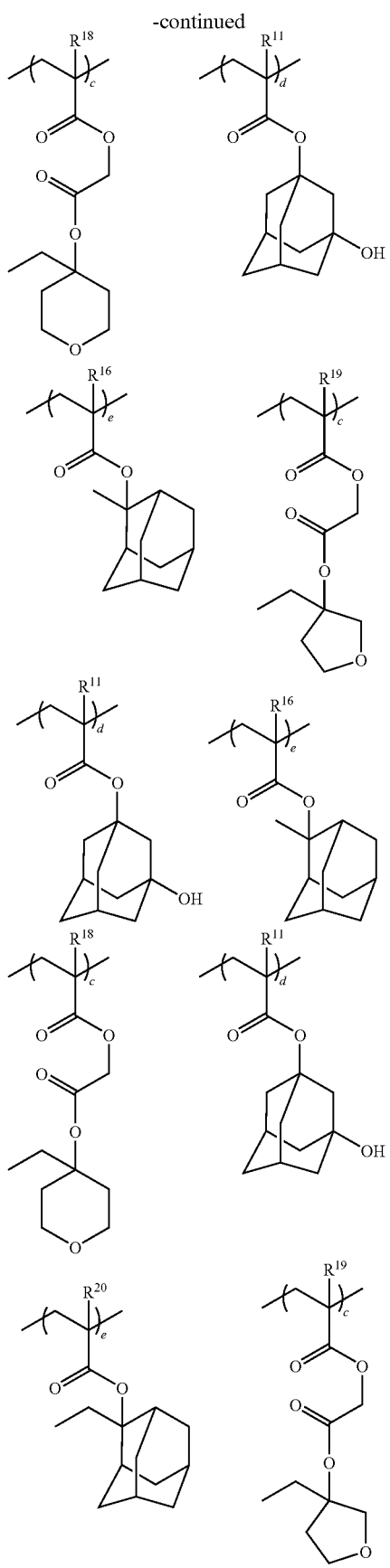
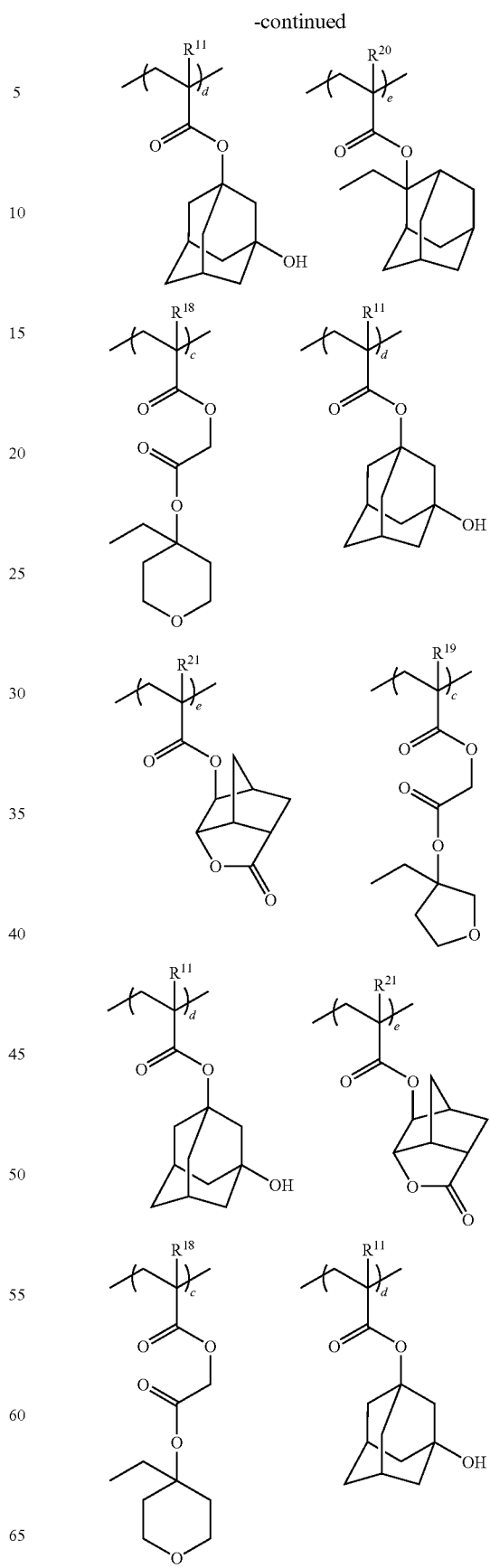

-continued

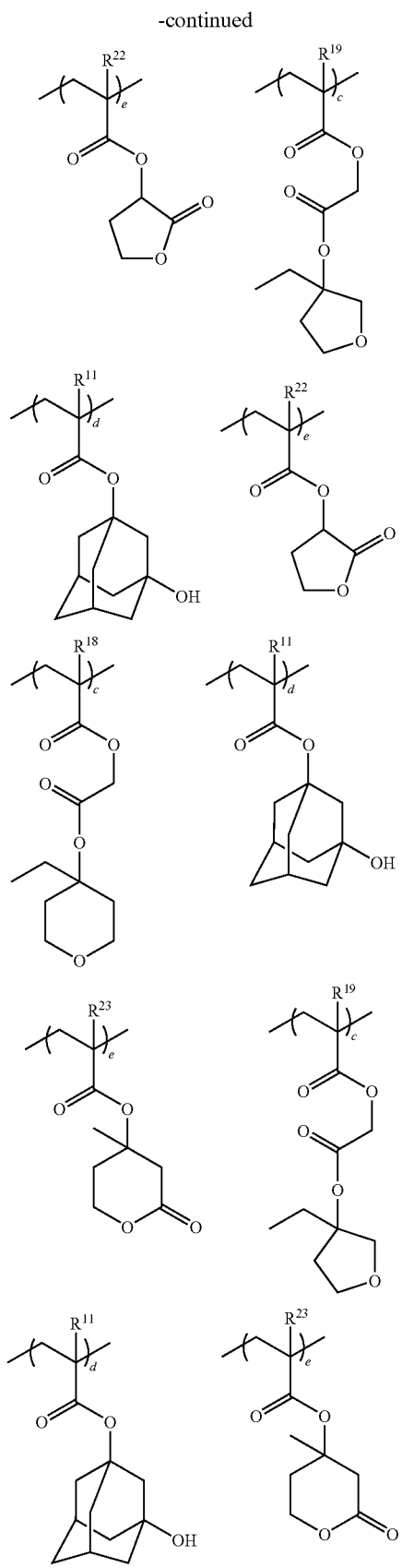
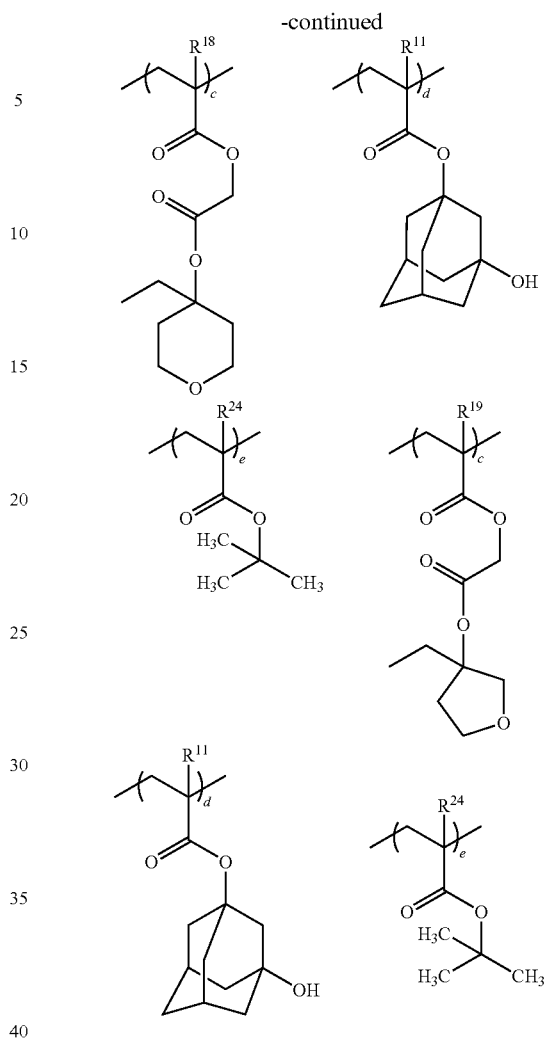

Though the polymer compound (4) is not particularly limited with respect to its weight average molecular weight (Mw), when it has a weight average molecular weight in the range of from 500 to 50,000, and preferably in the range of from 1,000 to 30,000, it is useful as a component of a photoresist composition as described later. In the present invention, such Mw and a number average molecular weight (Mn) can be determined by a gel permeation chromatography method (GPC method) using a column prepared by connecting two columns of TSK-gel SUPER HZM-H (a trade name, manufactured by Tosoh Corporation; diameter: 4.6 mm, length: 150 mm) and one column of TSK-gel SUPER HZ2000 (a trade name, manufactured by Tosoh Corporation; diameter: 4.6 mm, length: 150 mm) in series; using a differential refractometer as a detector and tetrahydrofuran as an eluting solution; measuring under a condition at a column temperature of 40° C., a temperature of the differential refractometer of 40° C. and a flow rate of the eluting solution of 0.35 mL/min; and calculating on the basis of a calibration curve prepared using standard polystyrene. Also, dispersity (Mw/Mn) is determined by dividing Mw by Mn.

A photoresist composition is prepared by blending the polymer compound (4) with a solvent and a photo acid generator as described later and optionally, a basic compound and an additive.

Examples of the solvent to be used for the photoresist composition include glycol ethers, for example, propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, etc.; esters, for example, ethyl lactate, methyl 3-methoxypropionate, methyl acetate, ethyl acetate, propyl acetate, etc.; ketones, for example, acetone, methyl ethyl ketone, methyl isopropyl ketone, methyl isobutyl ketone, methyl amyl ketone, cyclopentanone, cyclohexanone, etc.; and ethers, for example, diethyl ether, diisopropyl ether, dibutyl ether, tetrahydrofuran, 1,4-dioxane, etc. The solvent may be used singly or may be used in admixture of two or more kinds thereof.

The use amount of the solvent is usually in the range of from 1 to 50 parts by mass, and preferably in the range of from 2 to 25 parts by mass per part by mass of the polymer compound (4).

As the photo acid generator, photo acid generators which have hitherto been usually used for photoresists of a chemical amplification type can be used. Examples thereof include nitrobenzyl derivatives, for example, 2-nitrobenzyl p-toluenesulfonate, 2,6-dinitrobenzyl p-toluenesulfonate, 2,4-dinitrobenzyl p-toluenesulfonate, etc.; sulfonic acid esters, for example, 1,2,3-tris(methanesulfonyloxy)benzene, 1,2,3-tris(trifluoromethanesulfonyloxy)benzene, 1,2,3-tris(p-toluenesulfonyloxy)benzene, etc.; diazomethane derivatives, for example, bis(benzenesulfonyl)diazomethane, bis(p-toluenesulfonyl)diazomethane, bis(2,4-dimethylphenylsulfonyl)diazomethane, bis(1,1-dimethylethylsulfonyl)diazomethane, bis(cyclohexylsulfonyl)diazomethane, bis(n-butylsulfonyl)diazomethane, etc.; onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, 1,2'-naphthylcarbonylmethyltetrahydrothiophenium trifluoromethanesulfonate, etc.; glyoxime derivatives, for example, bis-O-(p-toluenensulfonyl)-α-dimethylglyoxime, bis-O-(n-butanesulfonyl)-α-dimethylglyoxime, etc.; sulfonic acid ester derivatives of an N-hydroxyimide compound, for example, N-hydroxysuccinimide methanesulfonic acid ester, N-hydroxysuccinimide trifluoromethanesulfonic acid ester, N-hydroxysuccinimide 1-propanesulfonic acid ester, N-hydroxyimide p-toluenesulfonic acid ester, N-hydroxynaphthalimide methanesulfonic acid ester, N-hydroxynaphthalimide benzenesulfonic acid ester, etc.; and halogen-containing triazine compounds, for example, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethy)-1,3,5-triazine, 2-[2-(3,5-dimethoxyphenyl)ethenyl]-4,6-bis(trichloromethyl)-1,3,5-triazine, etc. These photo acid generators may be used singly or may be used in admixture of two or more kinds thereof.

From the viewpoint of ensuring sensitivity and developability of the photoresist composition, in general, the use amount of the photo acid generator is preferably in the range of from 0.1 to 30 parts by mass, and more preferably in the range of from 0.5 to 10 parts by mass based on 100 parts by weight of the polymer compound (4).

For the purpose of suppressing a diffusion rate of an acid in a photoresist film to enhance a resolution, the photoresist composition of the present invention can be blended with a basic compound in an amount within the range where properties of the photoresist composition of the present invention are not adversely affected as the need arises. Examples of such a basic compound include amides, for example, formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butyl acrylamide, methylenebisacrylamide, methylenebismethacrylamide, N-methylolacrylamide, N-methoxyacrylamide, diacetone acrylamide, etc.; and amines, for example, pyridine, 2-methylpyridine, 4-methylpyridine, nicotine, quinoline, acridine, imidazole, 4-methylimidazole, benzimidazole, pyrazine, pyrazole, pyrrolidine, piperidine, tetrazole, morpholine, 4-methylmorpholine, piperazine, diazabicyclo[2,2,2]octane, tributylamine, tripentylamine, trihexylamine, triheptylamine, trioctylamine, triethanolamine, etc. These may be used singly or may be used in admixture of two or more kinds thereof. In case of using a basic compound, though the use amount thereof varies depending upon the kind of the basic compound, it is usually in the range of from 0.01 to 10 moles, and preferably in the range of from 0.05 to 1 mole per mole of the photo acid generator.

For the purpose of enhancing coating properties, if desired, the photosensitive composition of the present invention can be further blended with a surfactant in an amount in the range where properties of the photoresist composition of the present invention are not adversely affected.

Examples of the surfactant include polyoxyethylene lauryl ether, polyoxyethylene stearyl ether, polyoxyethylene oleyl ether and polyoxyethylene n-octylphenyl ether.

The surfactant may be used singly or may be used in admixture of two or more kinds thereof.

In case of using a surfactant, the use amount thereof is usually not more than 2 parts by mass based on 100 parts by mass of the polymer compound (4).

Furthermore, the photoresist composition of the present invention can be blended with other additives, for example, a sensitizer, an anti-halation agent, a shape improving agent, a storage stabilizer, an anti-foaming agent, etc. in an amount within the range where properties of the photoresist composition of the present invention are not adversely affected.

A prescribed resist pattern can be formed by coating the photoresist composition of the present invention on a substrate, prebaking usually at from 70 to 160° C. for 1 to 10 minutes, irradiating (exposing) with radiations via a prescribed mask, then post-exposure baking at from 70 to 160° C. for from 1 to 5 minutes to form a latent pattern and subsequently developing with a developing solution.

Examples of the developing solution include alkaline aqueous solutions having an inorganic base, for example, sodium hydroxide, potassium hydroxide, sodium carbonate, ammonia water, etc.; an alkylamine, for example, ethylamine, diethylamine, triethylamine, etc.; an alcoholamine, for example, dimethylethanolamine, triethanolamine, etc.; a quaternary ammonium salt, for example, tetramethylammonium hydroxide, tetraethylammonium hydroxide, etc.; or the like dissolved therein. Of these, an alkaline aqueous solution having a quaternary ammonium salt, for example, tetramethylammonium hydroxide, tetraethylammonium hydroxide, etc.

dissolved therein is preferably used. A concentration of the developing solution is usually in the range of from 0.1 to 20% by mass, and preferably in the range of from 0.1 to 10% by mass.

For the exposure, radiations having a wavelength of every kind, for example, ultraviolet rays, X-rays, etc. can be utilized. In the use for semiconductor resists, excimer lasers, for example, g-rays, i-rays, XeCl, KrF, KrCl, ArF, ArCl, etc. are usually used, and above all, an ArF excimer laser is preferably used from the viewpoint of micro fabrication. The exposure amount is preferably in the range of from 0.1 to 1,000 mJ/cm$^2$, and more preferably in the range of from 1 to 500 mJ/cm$^2$.

Also, the photoresist composition of the present invention can be applied to immersion lithography. The immersion lithography as referred to herein is an exposure technology for enhancing a resolution by injecting a liquid having a refractive index to light higher than air between a projection lens of an exposure device and a resist film.

EXAMPLES

The present invention is hereunder described in more detail with reference to the following Examples, but it should not be construed that the present invention is limited to these Examples.

A weight average molecular weight (Mw) and dispersity (Mw/Mn) were determined as a reduced value by a calibration curve prepared using standard polystyrene by using a differential refractometer as a detector by a gel permeation chromatography (GPC) method using tetrahydrofuran (THF) as an eluting solution. The GPC measurement was carried out by using a column prepared by connecting two columns of TSK-gel SUPER HZM-H (a trade name, manufactured by Tosoh Corporation; diameter: 4.6 mm, length: 150 mm) and one column TSK-gel SUPER HZ2000 (a trade name, manufactured by Tosoh Corporation; diameter: 4.6 mm, length: 150 mm) in series under a condition at a column temperature of 40° C., a temperature of the differential refractometer of 40° C. and a flow rate of the eluting solution of 0.35 mL/min.

Example 1

Synthesis of
4-methacryloyloxy-4-methyltetrahydropyran

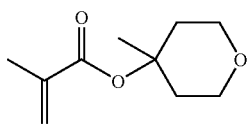

A three-necked flask having an inner volume of 100 mL, which was equipped with a thermometer, was charged with 3.48 g (30.0 mmoles) of 4-hydroxy-4-methyltetrahydropyran and 30.0 g of methylene chloride, and the inside of the flask was purged with nitrogen. This mixed solution was cooled with ice water; 4.40 mL (45.0 mmoles) of methacryloly chloride was subsequently added; and 6.27 mL (45.0 mmoles) of triethylamine was further added dropwise slowly while maintaining the temperature of the reaction solution at 2 to 5° C. After completion of the dropwise addition, stirring was continued at 4 to 5° C. for 3 hours. 20 mL of water and 20 mL of a saturated sodium hydrogencarbonate aqueous solution were successively added slowly to the obtained reaction mixed solution, and after stirring for a while, the mixture was allowed to stand, thereby separating it into an aqueous layer and an organic layer. The aqueous layer was extracted twice with 30 mL of methylene chloride; the extract was combined with the foregoing organic layer; the mixture was washed once with 10 mL of saturated salt water, dried over anhydrous magnesium sulfate and then concentrated in vacuo; and the obtained residue was purified by silica gel column chromatography (developing solvent: hexane/ethyl acetate=8/1 (volume ratio)), thereby obtaining 3.03 g (16.45 mmoles) of 4-methacryloyloxy-4-methyltetrahydropyran having the following physical properties as a colorless transparent liquid (purity: 99%, yield: 55%).

IR (KBr, cm$^{-1}$): 2965, 2857, 1712, 1635, 1137
$^1$H-NMR (300 MHz, CDCl$_3$, TMS, ppm) δ: 1.58 (3H, s), 1.68 to 1.78 (2H, m), 1.93 (3H, s), 2.20 (2H, d, J=9.6 Hz), 3.61 to 3.78 (4H, m), 5.54 (1H, s), 6.07 (1H, s)

Synthesis Example 1

Synthesis of
4-chloroacetoxy-4-methyltetrahydropyran

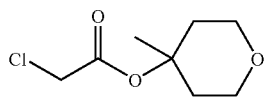

A four-necked flask having an inner volume of 100 mL, which was equipped with a dropping funnel, a thermometer and a nitrogen introducing pipe, was charged with 4.64 g (40.0 mmoles) of 4-hydroxy-4-methyltetrahydropyran and 20.0 g of methylene chloride and further charged with 0.24 g (2.0 mmoles) of 4-(N,N-dimethylamino)pyridine and 6.78 g (60.0 mmoles) of 2-chloroacetyl chloride. Subsequently, 6.37 g (63.0 mmoles) of triethylamine was added dropwise at room temperature over 30 minutes. After completion of the dropwise addition, the mixture was stirred at room temperature for 10 hours. To this reaction mixed solution, 1.11 g (24.0 mmoles) of ethanol was added dropwise, and subsequently, 20.0 g of water was added dropwise; and the mixture was stirred for 20 minutes. This reaction mixed solution was separated into an aqueous layer and an organic layer. The aqueous layer was extracted twice with 20 mL of methylene chloride; the extract was combined with the foregoing organic layer; the mixture was washed once with 10 mL of water and concentrated in vacuo, thereby obtaining 6.09 g (31.6 mmoles) of 4-chloroacetoxy-4-methyltetrahydropyran (yield: 79%).

$^1$H-NMR (300 MHz, CDCl$_3$, TMS, ppm) δ: 1.55 (3H, s), 1.65 to 1.79 (2H, m), 2.22 (2H, d, J=9.6 Hz), 3.60 to 3.77 (4H, m), 4.35 (2H, s)

Example 2

Synthesis of 4-methacryloyloxyacetoxy-4-methyltetrahydropyran

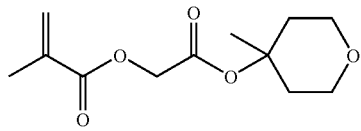

A four-necked flask having an inner volume of 50 mL, which was equipped with a thermometer and a nitrogen introducing pipe, was charged with 2.60 g (13.5 mmoles) of 4-chloroacetoxy-4-methyltetrahydropyran as obtained in the method of Synthesis Example 1, 1.31 g (9.46 mmoles) of potassium carbonate, 0.05 g (0.14 mmoles) of tetrabutylammonium iodide and 15 mL of toluene. To this mixed solution, 1.51 g (17.5 mmoles) of methacryloly was added dropwise at room temperature over 15 minutes. After completion of the dropwise addition, the mixture was heated at 50° C. and stirred for 4 hours. After cooling the reaction mixed solution to room temperature, 15 mL of water and 10 mL of ethyl acetate were added, thereby separating into an aqueous layer and an organic layer. The obtained organic layer was washed once with 5 mL of water, concentrated in vacuo and then purified by silica gel chromatography, thereby obtaining 2.22 g (9.2 mmoles) of 4-methacryloyloxyacetoxy-4-methyltetrahydropyran (yield: 68%).

$^1$H-NMR (300 MHz, CDCl$_3$, TMS, ppm) δ: 1.58 (3H, s), 1.63 to 1.79 (2H, m), 1.94 (3H, s), 2.18 (2H, d, J=9.6 Hz), 3.62 to 3.79 (4H, m), 5.13 (2H, s), 5.57 (1H, s), 6.11 (1H, s)

Example 3

Synthesis of Polymer Compound a

A four-necked flask having an inner volume of 100 mL, which was equipped with an electromagnetic stirrer, a reflux condenser and a thermometer, was charged with 3.45 g (18.7 mmoles) of 4-methacryloyloxy-4-methyltetrahydropyran as obtained in the method of Example 1, 2.96 g (12.5 mmoles) of 1-hydroxy-3-methacryloyloxyadamantane, 4.39 g (18.7 mmoles) of 2-methacryloyloxy-2-methyladanmantane, 35.4 g of methyl ethyl ketone and 0.66 g (4.0 mmoles) of 2,2'-azobisisobutyronitrile under a nitrogen atmosphere, and the mixture was subjected to a polymerization reaction at 80° C. for 4 hours. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 6.50 g of Polymer Compound a composed of the following constitutional unit. The obtained Polymer Compound a had an Mw of 6,500 and dispersity of 1.50.

Polymer Compound a:

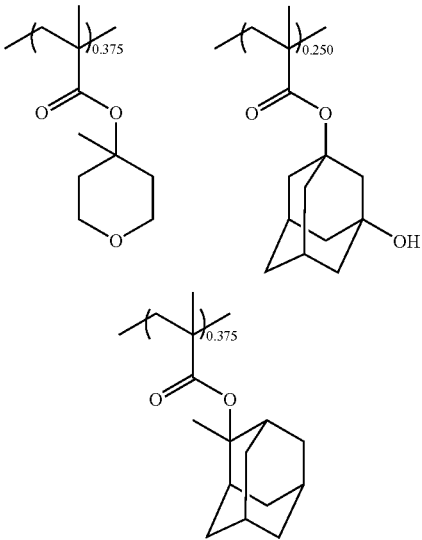

Example 4

Synthesis of Polymer Compound b

A polymerization reaction was carried out in the same charge amounts and under the same condition as in Example 3, except that in Example 3, 3.18 g (18.7 mmoles) of α-methacryloyloxy-γ-butyrolactone was used in place of 4.39 g (18.7 mmoles) of 2-methacryloyloxy-2-methyladamantane. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 6.22 g of Polymer Compound b composed of the following constitutional unit. The obtained Polymer Compound b had an Mw of 6,200 and dispersity of 1.55.

Polymer Compound b:

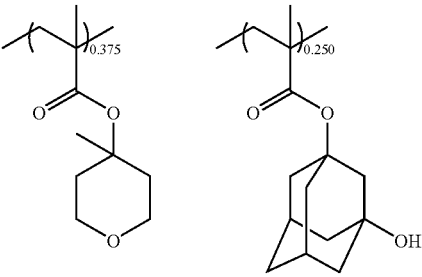

-continued

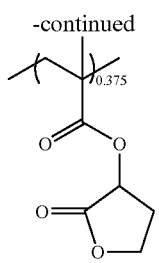

Example 5

Synthesis of Polymer Compound c

A polymerization reaction was carried out in the same charge amounts and under the same condition as in Example 4, except that in Example 4, 4.53 g (18.7 mmoles) of 4-methacryloyloxyacetoxy-4-methyltetrahydropyran as obtained in the method of Example 2 was used in place of 3.45 g (18.7 mmoles) of 4-methacryloyloxy-4-methyltetrahydropyran. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 5.99 g of Polymer Compound c composed of the following constitutional unit. The obtained Polymer Compound c had an Mw of 6,000 and dispersity of 1.61.

Polymer Compound c :

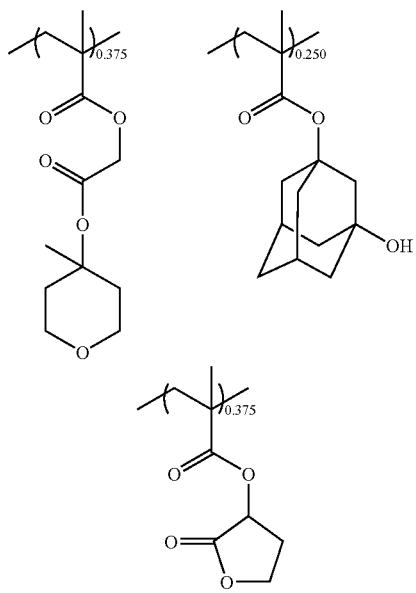

Synthesis Example 2

Synthesis of Polymer Compound d

A polymerization reaction was carried out in the same charge amounts and under the same condition as in Example 4, except that in Example 4, 4.39 g (18.7 mmoles) of 2-methacryloyloxy-2-methyladamantane was used in place of 3.45 g (18.7 mmoles) of 4-methacryloyloxy-4-methyltetrahydropyran. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 6.06 g of Polymer Compound d composed of the following constitutional unit. The obtained Polymer Compound d had an Mw of 10,000 and dispersity of 1.50.

Polymer Compound d :

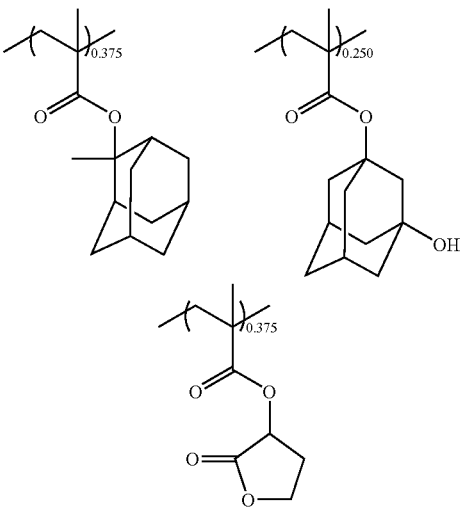

Synthesis Example 3

Synthesis of Polymer Compound e

A polymerization reaction was carried out in the same charge amounts and under the same condition as in Example 4, except that in Example 4, 3.18 g (18.7 mmoles) of 2-methacryloyloxytetrahydropyran was used in place of 3.45 g (18.7 mmoles) of 4-methacryloyloxy-4-methyltetrahydropyran. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 5.82 g of Polymer Compound e composed of the following constitutional unit. The obtained Polymer Compound e had an Mw of 6,500 and dispersity of 1.60.

Polymer Compound e :

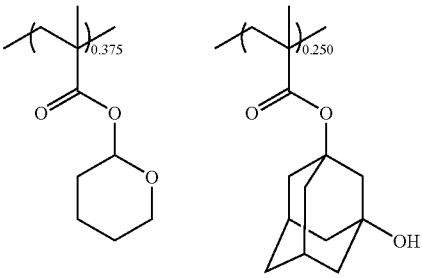

-continued

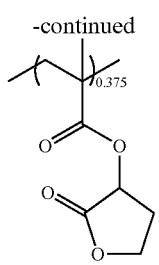

Synthesis Example 4

Synthesis of Polymer Compound f

A polymerization reaction was carried out in the same charge amounts and under the same condition as in Example 4, except that in Example 4, 3.41 g (18.7 mmoles) of 1-methacryloyloxy-1-methylcyclohexane was used in place of 3.45 g (18.7 mmoles) of 4-methacryloyloxy-4-methyltetrahydropyran. The obtained reaction mixed solution was added dropwise in methanol in an amount of about 20 times by mass at room temperature while stirring, thereby obtaining a white precipitate. The subject precipitate was collected by filtration and dried in vacuo (26.7 Pa) at 50° C. for 10 hours, thereby obtaining 5.69 g of Polymer Compound f composed of the following constitutional unit. The obtained Polymer Compound f had an Mw of 6,900 and dispersity of 1.58.

Polymer Compound f:

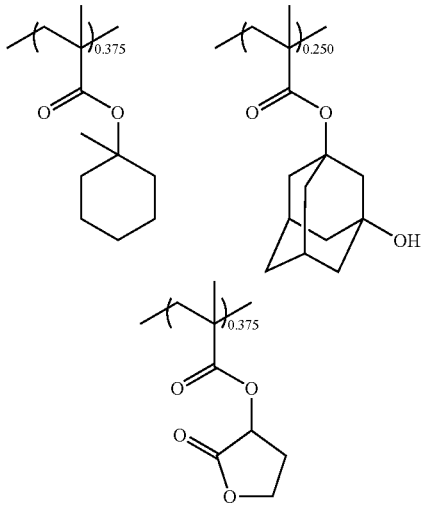

Examples 6 to 8 and Comparative Examples 1 to 3

Evaluation of Dissolution Properties 100 parts by mass of each of Polymer Compounds a, b, c, d, e and f as obtained in Examples 3 to 5 and Synthesis Examples 2 to 4, 3 parts by mass of TPS-109 (a trade name, manufactured by Midori Kagaku Co., Ltd.) as a photo acid generator and a solvent (mixed solvent of propylene glycol monomethyl ether acetate/ethyl lactate=1/1) were mixed to prepare six kinds of photoresist compositions each having a concentration of the polymer compound of 12% by mass. These photoresist compositions were each filtered using a filter [made of a tetrafluoroethylene resin (PTFE), pore size: 0.2 μm] and then coated on a quartz substrate of 1 inch in size on the surface of which had been vacuum vapor deposited a gold electrode by a spin coating method, thereby forming a photosensitive layer having a thickness of about 300 nm. These quartz substrates were each prebaked on a hot plate at 110° C. for 90 seconds, thereafter exposed with an ArF excimer laser (wavelength: 193 nm) at an exposure amount of 100 mJ/cm$^2$ and subsequently post-exposure baked at 110° C. for 90 seconds. The foregoing quartz substrate was set in a quartz crystal microbalance device "RQCM" (a trade name, manufactured by Maxtek, Inc.) and developed with a 2.38% by mass tetramethylammonium hydroxide aqueous solution for 120 seconds. A change in frequency of the quartz substrate during the development treatment was monitored with a lapse of time; and thereafter, the obtained change in frequency was reduced into a change in thickness of the photosensitive layer, thereby calculating a maximum amount of swelling from the change of increase in thickness and a dissolution rate from the change of decrease in thickness, respectively. The results are shown in Table 1.

Examples 9 to 11 and Comparative Examples 4 to 6

Evaluation of Exposure 100 parts by mass of each of Polymer Compounds a, b, c, d, e and f as obtained in Examples 3 to 5 and Synthesis Examples 2 to 4, 3 parts by mass of TPS-109 (a trade name, manufactured by Midori Kagaku Co., Ltd.) as a photo acid generator and a solvent (mixed solvent of propylene glycol monomethyl ether acetate/ethyl lactate=1/1) were mixed to prepare six kinds of photoresist compositions each having a concentration of the polymer compound of 12% by mass. These photoresist compositions were each filtered using a filter [made of a tetrafluoroethylene resin (PTFE), pore size: 0.2 μm]. On a silicon wafer having a diameter of 10 cm on which an antireflection film (base film) having a thickness of about 100 nm had been formed by coating a propylene glycol monomethyl ether acetate solution of a cresol/novolak resin (PS-6937, manufactured by Gun Ei Chemical Industry Co., Ltd.) in a concentration of 6% by mass by a spin coating method and baking on a hot plate at 200° C. for 90 seconds, each of the subject filtrates was coated by a spin coating method and prebaked on a hot plate at 130° C. for 90 seconds, thereby forming a resist film having a thickness of about 300 nm. This resist film was exposed with an ArF excimer laser having a wavelength of 193 nm by a double beam interference method. Subsequently, the exposed resist film was post-exposure baked at 130° C. for 90 seconds and then developed with a 2.38% by mass tetramethylammonium hydroxide aqueous solution for 60 seconds, thereby forming a 1:1 line-and-space pattern having a line width of 100 nm. A piece obtained by cleaving and cutting the developed wafer was observed by a scanning electron microscope (SEM), thereby carrying out shape observation of the resist pattern and measurement of LWR. As to LWR, a line width was detected at plural positions within a measuring monitor, and a 3σ value (σ: standard deviation) of that line width was defined as an index. The results are shown in Table 2.

Examples 12 to 14 and Comparative Examples 7 to 9

Evaluation of Storage Stability 100 parts by mass of each of Polymer Compounds a, b, c, d, e and f as obtained in Examples 3 to 5 and Synthesis Examples 2 to 4, 3 parts by mass of TPS-109 (a trade name, manufactured by Midori Kagaku Co., Ltd.) as a photo acid generator and a solvent (mixed solvent of propylene glycol monomethyl ether acetate/ethyl lactate=1/1) were mixed to prepare six kinds of photoresist compositions each having a concentration of the polymer compound of 12% by mass.

These photoresist compositions were each filtered using a filter [made of a tetrafluoroethylene resin (PTFE), pore size; 0.2 μm]. This filtrate was stored at 30° C. for one month, and thereafter, shape observation of the resist pattern and measurement of LWR were carried out in the same manner as in Examples 9 to 11 and Comparative Examples 4 to 6.

TABLE 1

| | | Evaluation of dissolution properties | |
|---|---|---|---|
| | Used polymer compound | Dissolution rate at development (nm/sec) | Maximum amount of swelling (nm) |
| Example 6 | Polymer Compound a 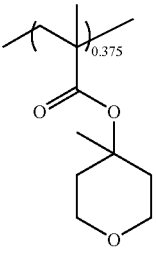 | 900 | 8 |
| Example 7 | Polymer Compound b 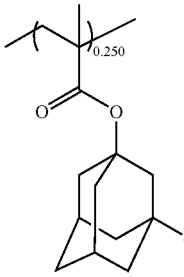 | 1230 | 6 |
| Example 8 | Polymer Compound c 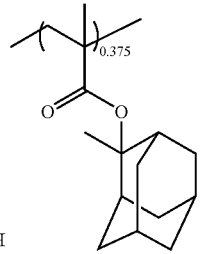 | 1380 | 6 |

TABLE 1-continued

| | | Evaluation of dissolution properties | |
|---|---|---|---|
| | Used polymer compound | Dissolution rate at development (nm/sec) | Maximum amount of swelling (nm) |
| Comparative Example 1 | Polymer Compound d | 60 | 40 |
| Comparative Example 2 | Polymer Compound e | 1100 | 10 |
| Comparative Example 3 | Polymer Compound f | 530 | 19 |

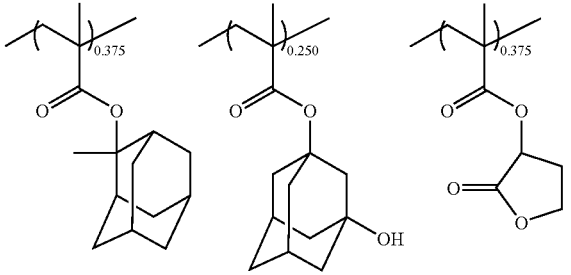

TABLE 2

| | | Evaluation of exposure | |
|---|---|---|---|
| | Used polymer compound | LWR (nm) | Pattern shape |
| Example 9 | Polymer Compound a | 8.0 | Good |

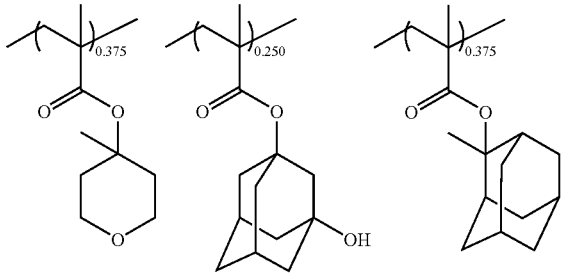

TABLE 2-continued
| | Evaluation of exposure | | |
|---|---|---|---|
| | Used polymer compound | LWR (nm) | Pattern shape |
| Example 10 | Polymer Compound b 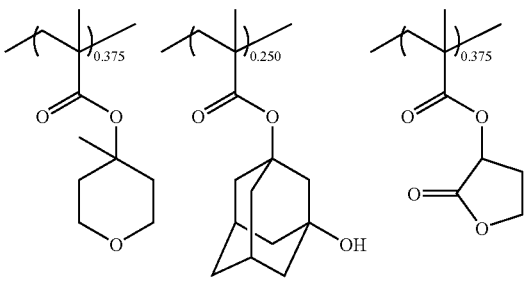 | 7.7 | Good |
| Example 11 | Polymer Compound c 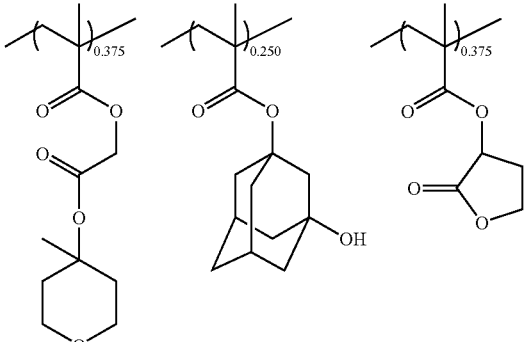 | 7.5 | Good |
| Comparative Example 4 | Polymer Compound d 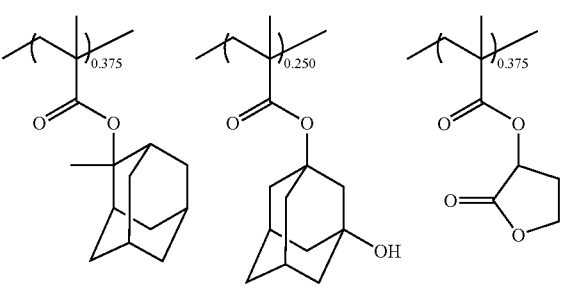 | 12.3 | Good |
| Comparative Example 5 | Polymer Compound e 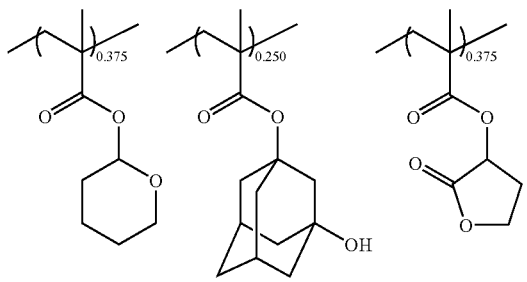 | 8.5 | Good |

TABLE 2-continued
| | Evaluation of exposure | | |
|---|---|---|---|
| | Used polymer compound | LWR (nm) | Pattern shape |
| Comparative Example 6 | Polymer Compound f | 10.3 | Good |
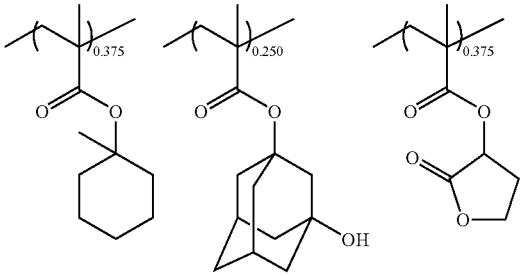
TABLE 3
| | Evaluation of storage stability | | |
|---|---|---|---|
| | Used polymer compound | LWR (nm) | Pattern shape |
| Example 12 | Polymer Compound a | 8.0 | Good |
| Example 13 | Polymer Compound b | 7.8 | Good |

TABLE 3-continued

| | Evaluation of storage stability | | |
|---|---|---|---|
| | Used polymer compound | LWR (nm) | Pattern shape |
| Example 14 | Polymer Compound c 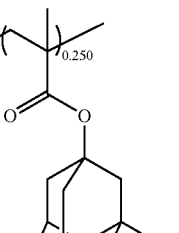 | 7.8 | Good |
| Comparative Example 7 | Polymer Compound d 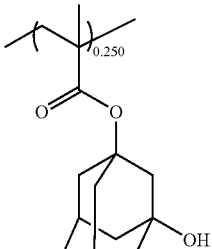 | 13.2 | Good |
| Comparative Example 8 | Polymer Compound e 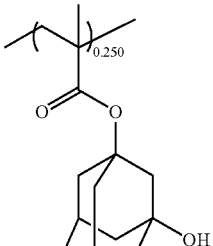 | Impossible to measure | Poor |
| Comparative Example 9 | Polymer Compound f 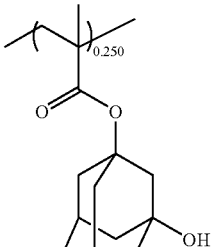 | 10.5 | Good |

It is understood from the foregoing results that in the case of a polymer compound having the tertiary alcohol derivative (1) of the present invention as a constitutional unit (Polymer Compounds a to c), the dissolution rate in an alkaline developing solution is very high, and the maximum amount of swelling at the development is very small (see Examples 6 to 8 and Comparative Examples 1 to 3); and LWR is improved (see Examples 9 to 11 and Comparative Examples 4 to 6) as compared with the case of a polymer compound not having the tertiary alcohol derivative (1) (Polymer Compounds d to e). Also, in view of the matter that the storage stability is high (see Examples 12 to 14 and Comparative Examples 7 to 9), it is understood that the present invention is useful as a photoresist composition for manufacturing an electronic device.

INDUSTRIAL APPLICABILITY

The tertiary alcohol derivative (1) and the polymer compound (4) of the present invention are useful as a raw material of a photoresist composition. Also, the photoresist composition of the present invention is useful as a photoresist composition for manufacturing an electronic device.

The invention claimed is:

1. A tertiary alcohol derivative represented by the following general formula (1):

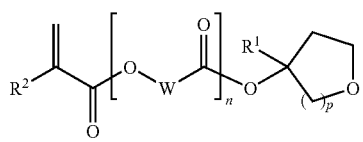

(wherein $R^1$ represents a linear alkyl group having from 1 to 6 carbon atoms, a branched alkyl group having from 3 to 6 carbon atoms or a cyclic alkyl group having from 3 to 6 carbon atoms; $R^2$ represents a hydrogen atom or a methyl group; W represents a linear alkylene group having from 1 to 10 carbon atoms, a branched alkylene group having from 3 to 10 carbon atoms or a cyclic alkylene group having from 3 to 10 carbon atoms; n represents 0 or 1; and p represents 1 or 2).

2. The tertiary alcohol derivative according to claim 1, wherein W is a methylene group or a 1,1-ethanediyl group.

3. The tertiary alcohol derivative according to claim 1, wherein n is 0.

4. A polymer compound obtained by polymerizing the tertiary alcohol derivative according to claim 1 as one of raw materials.

5. A photoresist composition comprising the polymer compound according to claim 4 and a photo acid generator.

* * * * *